United States Patent
Sugiyama et al.

(10) Patent No.: US 10,899,790 B2
(45) Date of Patent: Jan. 26, 2021

(54) METHOD FOR MODIFYING T CELL POPULATION

(71) Applicants: OSAKA UNIVERSITY, Suita (JP); KNC LABORATORIES CO., LTD., Kobe (JP)

(72) Inventors: Haruo Sugiyama, Suita (JP); Fumihiro Fujiki, Suita (JP); Masahiro Neya, Kobe (JP); Shinya Kohno, Kobe (JP)

(73) Assignees: OSAKA UNIVERSITY, Suita (JP); KNC LABORATORIES CO., LTD., Kobe (JP)

(*) Notice: Subject to any disclaimer, the term of this patent is extended or adjusted under 35 U.S.C. 154(b) by 0 days.

(21) Appl. No.: 16/347,337

(22) PCT Filed: Nov. 8, 2017

(86) PCT No.: PCT/JP2017/040302
§ 371 (c)(1),
(2) Date: May 3, 2019

(87) PCT Pub. No.: WO2018/088439
PCT Pub. Date: May 17, 2018

(65) Prior Publication Data
US 2019/0284228 A1    Sep. 19, 2019

(30) Foreign Application Priority Data
Nov. 9, 2016 (JP) ................. 2016-219099

(51) Int. Cl.
| | | |
|---|---|---|
| *C07J 63/00* | (2006.01) | |
| *A61P 35/00* | (2006.01) | |
| *A61K 31/16* | (2006.01) | |
| *A61K 31/166* | (2006.01) | |
| *A61K 31/196* | (2006.01) | |
| *A61K 31/215* | (2006.01) | |
| *A61K 31/216* | (2006.01) | |
| *A61K 31/265* | (2006.01) | |
| *A61K 31/27* | (2006.01) | |
| *A61K 31/40* | (2006.01) | |
| *A61K 31/445* | (2006.01) | |
| *A61K 31/5375* | (2006.01) | |
| *C12N 5/0783* | (2010.01) | |
| *A61K 31/19* | (2006.01) | |
| *A61P 37/04* | (2006.01) | |
| *A61P 31/00* | (2006.01) | |
| *A61K 31/44* | (2006.01) | |

(52) U.S. Cl.
CPC ............ *C07J 63/008* (2013.01); *A61K 31/16* (2013.01); *A61K 31/166* (2013.01); *A61K 31/19* (2013.01); *A61K 31/196* (2013.01); *A61K 31/215* (2013.01); *A61K 31/216* (2013.01); *A61K 31/265* (2013.01); *A61K 31/27* (2013.01); *A61K 31/40* (2013.01); *A61K 31/44* (2013.01); *A61K 31/445* (2013.01); *A61K 31/5375* (2013.01); *A61P 31/00* (2018.01); *A61P 35/00* (2018.01); *A61P 37/04* (2018.01); *C07J 63/00* (2013.01); *C12N 5/0636* (2013.01); *C12N 2501/39* (2013.01)

(58) Field of Classification Search
CPC ............................ C07J 63/008; C12N 5/0636
See application file for complete search history.

(56) References Cited

U.S. PATENT DOCUMENTS

| | | |
|---|---|---|
| 3,311,613 A | 3/1967 | McFarlane et al. |
| 7,420,034 B2 | 9/2008 | Sugiyama et al. |
| 7,622,119 B2 | 11/2009 | Sugiyama |
| 7,666,985 B2 | 2/2010 | Sugiyama et al. |
| 8,388,975 B2 | 3/2013 | Sugiyama |
| 8,476,315 B2 | 7/2013 | Kosma et al. |
| 8,759,483 B2 | 6/2014 | Sugiyama |
| 8,778,350 B2 | 7/2014 | Sugiyama |
| 8,933,038 B2 | 1/2015 | Sugiyama |
| 8,945,578 B2 | 2/2015 | Sugiyama |
| 8,968,745 B2 | 3/2015 | Sugiyama |
| 9,796,751 B2 | 10/2017 | Takeuchi et al. |
| 2003/0032078 A1 | 2/2003 | Travis |
| 2003/0119715 A1 | 6/2003 | Ward et al. |
| 2007/0082860 A1 | 4/2007 | Sugiyama et al. |

(Continued)

FOREIGN PATENT DOCUMENTS

| | | |
|---|---|---|
| CN | 102656263 A | 9/2012 |
| EP | 2 471 901 A1 | 7/2012 |

(Continued)

OTHER PUBLICATIONS

Abe et al., Interferon induction by glycyrrhizin and glycyrrhetinic acid in mice. Microbiology and Immunology, 26(6), 535-539 Abstract (Year: 1982).*

(Continued)

*Primary Examiner* — Barbara P Badio
(74) *Attorney, Agent, or Firm* — Oblon, McClelland, Maier & Neustadt, L.L.P.

(57) ABSTRACT

Provided are: a compound represented by formula (I); a retinoid metabolic pathway inhibitor comprising the same; an agent for increasing the ratio of memory T cells; a prophylactic and/or therapeutic agent for cancer or an infectious disease; a cancer immunotherapeutic adjuvant; an immunopotentiator; and a method for preparing a T cell population wherein the ratio of memory T cells is increased, said method comprising using the compound of formula (I).

11 Claims, 3 Drawing Sheets
Specification includes a Sequence Listing.

(56) References Cited

U.S. PATENT DOCUMENTS

| | | |
|---|---|---|
| 2008/0152631 A1 | 6/2008 | Sugiyama |
| 2009/0076032 A1 | 3/2009 | Ward et al. |
| 2009/0099090 A1 | 4/2009 | Sugiyama et al. |
| 2009/0136470 A1 | 5/2009 | Cheroutre et al. |
| 2010/0062013 A1 | 3/2010 | Sugiyama |
| 2010/0113610 A1 | 5/2010 | Kim et al. |
| 2010/0292160 A1 | 11/2010 | Sugiyama |
| 2012/0022154 A1 | 1/2012 | Classenhouben et al. |
| 2012/0142109 A1 | 6/2012 | Katayama et al. |
| 2012/0195918 A1 | 8/2012 | Sugiyama |
| 2013/0196427 A1 | 8/2013 | Sugiyama |
| 2013/0266958 A1 | 10/2013 | Sugiyama et al. |
| 2014/0193442 A1 | 7/2014 | Sugiyama |
| 2014/0193443 A1 | 7/2014 | Sugiyama |
| 2014/0199332 A1 | 7/2014 | Sugiyama |
| 2016/0376303 A1 | 12/2016 | Takeuchi et al. |
| 2017/0369841 A1 | 12/2017 | Sugiyama et al. |

FOREIGN PATENT DOCUMENTS

| | | |
|---|---|---|
| GB | 1046413 A | 10/1966 |
| JP | 2004-506691 A | 3/2004 |
| JP | 2009-529572 A | 8/2009 |
| JP | 2010-531138 A | 9/2010 |
| WO | WO 02/15920 A2 | 2/2002 |
| WO | WO 03/106682 A1 | 12/2003 |
| WO | WO 2005/095598 A1 | 10/2005 |
| WO | WO 2007/097358 A1 | 8/2007 |
| WO | WO 2007/105015 A2 | 9/2007 |
| WO | WO 2008/137488 A1 | 11/2008 |
| WO | WO 2008/157394 A2 | 12/2008 |
| WO | WO 2010/103046 A1 | 9/2010 |
| WO | WO 2011/024791 A1 | 3/2011 |
| WO | WO 2012/046730 A1 | 4/2012 |
| WO | WO 2015/076325 A1 | 5/2015 |
| WO | WO 2016/104486 A1 | 6/2016 |

OTHER PUBLICATIONS

Ijichi et al., Molecular Design of Sweet Tasting Compounds Based on 3beta-amino-3beta-deoxy-18beta-glycerrhetinic Acid: Amindo Functionality Eliciting Tremendous Sweetness. Chemistry Letters, vol. 34(3), pp. 356-357 (Year: 2005).*
European Office Action dated Aug. 14, 2019, in Patent Application No. 15 873 054.9, 5 pages.
U.S. Appl. No. 15/537,927, filed Jul. 26, 2017, US 2017-0369841 A1, Haruo Sugiyama.
International Search Report dated Jan. 9, 2018 in PCT/JP2017/040302, 3 pages.
International Preliminary Report on Patentability dated May 14, 2019 in PCT/JP2017/040302, 10 pages (submitting English translation only).
Office Action dated Oct. 19, 2018 in U.S. Appl. No. 15/537,927, 16 pages.
Office Action dated Jul. 9, 2019 in U.S. Appl. No. 15/537,927, 15 pages.
International Search Report dated Feb. 16, 2016 in PCT/JP2015/085793, 3 pages.
International Preliminary Report on Patentability dated Jul. 6, 2017 in PCT/JP2015/085793, 9 pages (submitting English translation only).
Extended European Search Report dated Aug. 23, 2018 in Patent Application No. 15873054.9, 9 pages.
Heller, L. et al. "First Occurrence of a Furano-glycyrrhetinoate and Its Cytotoxicity" Archiv der Pharmazie, vol. 348, No. 12, 2015, 8 pages.
Csuk, R. et al. "Synthesis and antitumor activity of ring A modified glycyrrhetinic acid derivatives" European Journal of Medicinal Chemistry, vol. 46, No. 11, 2011, 14 pages.
Csuk, R. et al. "Synthesis and Cytotoxic Activity of Methyl Glycyrrhetinate Esterified with Amino Acids" Zeitschrift für Naturforschung B: A Journal of Chemical Sciences, 2012, vol. 67, Issue 7, pp. 731-746.
Zou, L-W. et al. "Design, synthesis, and structure-activity relationship study of glycyrrhetinic acid derivatives as potent and selective inhibitors against human carboxylesterase 2" European Journal of Medicinal Chemistry, vol. 112, 2016, 9 pages.
Beseda, I. et al. "Synthesis of glycyrrhetinic acid derivatives for the treatment of metabolic diseases" Bioorganic & Medicinal Chemistry, vol. 18, No. 1, 2010, 22 pages.
Kim, H-O. et al. "Triterpenoids. XXVIII. Leuckart reaction with glycyrrhetic acid derivatives" Izvestiya Akademii Nauk Kazakhskoi SSR, Seriya Khimicheskaya, vol. 22, No. 5, 1972, 4 pages.
Tolstikov, G.A. et al. "Carbon-13 NMR spectra of a series of penta- and hexacyclic triterpenoids glycyrrhetic acid derivatives" Khimiya Prirodnykh Soedinenii, No. 5, 1985, 16 pages (with English abstract from the corresponding English article).
Ijichi, S. et al. "Molecular Design of Sweet Tasting Compounds Based on 3β-Amino-3β-deoxy-18β-glycyrrhetinic Acid: Amido Functionality Eliciting Tremendous Sweetness" Chemistry Letters, vol. 34, No. 3, 2015, 2 pages.
Oka, Y. et al. "Human cytotoxic T-lymphocyte responses specific for peptides of the wild-type Wilms' tumor gene (WT1) product" Immunogenetics, vol. 51, No. 2, 2000, 9 pages.
Tan, X. et al. "Retinoic Acid as a Vaccine Adjuvant Enhances CD8$^+$ T Cell Response and Mucosal Protection from Viral Challenge" Journal of Virology, vol. 85, No. 16, 2011, 12 pages.
Furugaki, K. et al. "DNA vaccination with all-trans retinoic acid treatment Induces long-term survival and elicits specific immune responses requiring CD4$^+$ and CD8$^+$ T-Cell activation in an acute promyelocytic leukemia mouse model" Blood, vol. 115, No. 3, 2010, 5 pages.
Galvin, K.C. et al. "Blocking retinoic acid receptor-α enhances the efficacy of a dendritic cell vaccine against tumours by suppressing the induction of regulatory T cells" Cancer Immunol Immunother, vol. 62, 2013, 10 pages.
Allie, S.R. et al. "Critical Role for All-trans Retinoic Acid for Optimal Effector and Effector Memory CD8 T Cell Differentiation" The Journal of Immunology, vol. 190, 2013, 11 pages.
Napoli, J.L. "Physiological insights into all-trans-retinoic acid biosynthesis" Biochimica et Biophysica Acta, vol. 1821, 2012 16 pages.
Combined Chinese Office Action and Search Report dated Jan. 10, 2020 in Chinese Patent Application No. 201580070889.3 (with English translation), 21 pages.
Indian Office Action dated Feb. 26, 2020 in Indian Patent Application No. 201747025434, 5 pages.
Cammas, L., et al., "Expression of the murine retinol dehydrogenase 10 (Rdh10) gene correlates with many sites of retinoid signalling during embryogenesis and organ differentiation", Developmental Dynamics, Oct. 2007, vol. 236, pp. 2899-2908.
Yifeng, H., et al., "Cancer-associated CD8 +memory T cells in the application of adoptive immunotherapy", Chinese Journal of Cancer Biotherapy, 2012, vol. 19, Issue 2, pp. 116-121 (with English abstract).
Extended European Search Report dated Apr. 6, 2020 in European Patent Application No. 17870242.9.
Office Action dated Sep. 4, 2020 in Chinese patent application No. 201580070889.3 (with English Translation).

* cited by examiner

SEQUENCE LISTING

<160> NUMBER OF SEQ ID NOS: 5

<210> SEQ ID NO 1
<211> LENGTH: 341
<212> TYPE: PRT
<213> ORGANISM: Homo sapiens

<400> SEQUENCE: 1

Met Asn Ile Val Val Glu Phe Phe Val Val Thr Phe Lys Val Leu Trp
1               5                   10                  15

Ala Phe Val Leu Ala Ala Ala Arg Trp Leu Val Arg Pro Lys Glu Lys
            20                  25                  30

Ser Val Ala Gly Gln Val Cys Leu Ile Thr Gly Ala Gly Ser Gly Leu
        35                  40                  45

Gly Arg Leu Phe Ala Leu Glu Phe Ala Arg Arg Arg Ala Leu Leu Val
    50                  55                  60

Leu Trp Asp Ile Asn Thr Gln Ser Asn Glu Glu Thr Ala Gly Met Val
65                  70                  75                  80

Arg His Ile Tyr Arg Asp Leu Glu Ala Ala Asp Ala Ala Ala Leu Gln
            85                  90                  95

Ala Gly Asn Gly Glu Glu Ile Leu Pro His Cys Asn Leu Gln Val
            100                 105                 110

Phe Thr Tyr Thr Cys Asp Val Gly Lys Arg Glu Asn Val Tyr Leu Thr
        115                 120                 125

Ala Glu Arg Val Arg Lys Glu Val Gly Glu Val Ser Val Leu Val Asn
130                 135                 140

Asn Ala Gly Val Val Ser Gly His His Leu Leu Glu Cys Pro Asp Glu
145                 150                 155                 160

Leu Ile Glu Arg Thr Met Met Val Asn Cys His Ala His Phe Trp Thr
                165                 170                 175

Thr Lys Ala Phe Leu Pro Thr Met Leu Glu Ile Asn His Gly His Ile
            180                 185                 190

Val Thr Val Ala Ser Ser Leu Gly Leu Phe Ser Thr Ala Gly Val Glu
        195                 200                 205

Asp Tyr Cys Ala Ser Lys Phe Gly Val Val Gly Phe His Glu Ser Leu
    210                 215                 220

Ser His Glu Leu Lys Ala Ala Glu Lys Asp Gly Ile Lys Thr Thr Leu
225                 230                 235                 240

Val Cys Pro Tyr Leu Val Asp Thr Gly Met Phe Arg Gly Cys Arg Ile
                245                 250                 255

Arg Lys Glu Ile Glu Pro Phe Leu Pro Pro Leu Lys Pro Asp Tyr Cys
            260                 265                 270

Val Lys Gln Ala Met Lys Ala Ile Leu Thr Asp Gln Pro Met Ile Cys
        275                 280                 285

Thr Pro Arg Leu Met Tyr Ile Val Thr Phe Met Lys Ser Ile Leu Pro
    290                 295                 300

Phe Glu Ala Val Val Cys Met Tyr Arg Phe Leu Gly Ala Asp Lys Cys
305                 310                 315                 320

Met Tyr Pro Phe Ile Ala Gln Arg Lys Gln Ala Thr Asn Asn Asn Glu
                325                 330                 335

Ala Lys Asn Gly Ile
            340

<210> SEQ ID NO 2
<211> LENGTH: 3981
<212> TYPE: DNA
<213> ORGANISM: Homo sapiens
<220> FEATURE:
<221> NAME/KEY: CDS
<222> LOCATION: (689)..(1714)

<400> SEQUENCE: 2
agagccggcc cggagcgctc tgacttgcaa gcgggctgcg ctgcggagcc cagtgcccga      60
gtgacacccg cggagagtgc agggccgggg aacgcgagcc ctcggggca gctgcaaggc     120 gttgggcagc gcttgcctgc gccgagcgag tctcccttc ccggcgctcc gccgccccgc     180
accccactct cccaccctct cgcaacttgg gtcgagttga caactcccgc ggcagccccgc    240 tggcccgtgc cgcctccgct gcgcacccct ccccgggt gagagggagc cggcgcgccg      300
gttccgggga cgctcgggcg gcagcagctt ggccatgagg gcagttcgag tagtctaact    360
cgcggctgtc accgccactg cagcggagcc ggccggccgg gcgctgcggg acgggcgggc    420
ggctgccggc aggaggcgcc gagccgggtg actgccgcgg cgggcacagt ccggggccac    480
agcgccgagc ccgggcggga gtggccccgc gcaggcaggg agcggcgccg cgcactccaa    540
cccggcgggc acctcggggg cgggcgcggg gcgcagcctt ctcgtcccgg cctctgtgac    600

-continued

```
aagcgccccg gagccgggag cccgattgcc gggctcgggg tgggcgcgga cgcaggcact         660
gggctcgtgc ggggccccgg gcgtcgcg atg aac atc gtg gtg gag ttc ttc           712
                                Met Asn Ile Val Val Glu Phe Phe
                                  1               5 gtg gtc act ttc aaa gtg ctc tgg gcg ttc gtg ctg gcc gcg gcg cgc          760
Val Val Thr Phe Lys Val Leu Trp Ala Phe Val Leu Ala Ala Ala Arg
         10              15                  20 tgg ctg gtg cgg ccc aag gag aag agc gtg gcg ggc cag gtg tgc ctc          808
Trp Leu Val Arg Pro Lys Glu Lys Ser Val Ala Gly Gln Val Cys Leu
 25              30                  35                  40 atc acc ggc gcc ggc agc ggc ctg ggc cgc ctc ttc gcg ctg gag ttc          856
Ile Thr Gly Ala Gly Ser Gly Leu Gly Arg Leu Phe Ala Leu Glu Phe
                 45                  50                  55 gcc cgg cgt cgg gcg ctg ctg gtg ctg tgg gac atc aac acg caa agc          904
Ala Arg Arg Arg Ala Leu Leu Val Leu Trp Asp Ile Asn Thr Gln Ser
 60                  65                  70 aac gag gag acg gct ggc atg gtg cgc cac atc tac cgc gac ctg gag          952
Asn Glu Glu Thr Ala Gly Met Val Arg His Ile Tyr Arg Asp Leu Glu
         75                  80                  85 gcg gcc gac gcc gct gcg ctg caa gct ggg aat ggt gag gaa gaa att         1000
Ala Ala Asp Ala Ala Ala Leu Gln Ala Gly Asn Gly Glu Glu Glu Ile
 90                  95                 100 ctg ccc cac tgt aac ttg cag gtt ttt acc tac acc tgt gac gtg ggg         1048
Leu Pro His Cys Asn Leu Gln Val Phe Thr Tyr Thr Cys Asp Val Gly
105                 110                 115                 120 aag agg gag aac gtc tac ctg acg gct gaa aga gtc cgc aag gag gtt         1096
Lys Arg Glu Asn Val Tyr Leu Thr Ala Glu Arg Val Arg Lys Glu Val
                125                 130                 135 ggc gaa gtc tca gtc ctg gtc aat aat gct ggt gtg gtc tct ggg cat         1144
Gly Glu Val Ser Val Leu Val Asn Asn Ala Gly Val Val Ser Gly His
                140                 145                 150 cac ctt ctg gaa tgt cct gat gag ctc att gag aga acc atg atg gtc         1192
His Leu Leu Glu Cys Pro Asp Glu Leu Ile Glu Arg Thr Met Met Val
                155                 160                 165 aat tgc cat gca cac ttc tgg acc act aag gct ttt ctt cct acg atg         1240
Asn Cys His Ala His Phe Trp Thr Thr Lys Ala Phe Leu Pro Thr Met
170                 175                 180 ctg gag att aat cat ggt cat att gtg aca gtt gca agt tcc ttg gga         1288
Leu Glu Ile Asn His Gly His Ile Val Thr Val Ala Ser Ser Leu Gly
185                 190                 195                 200 ttg ttc agt act gcc gga gtt gag gat tac tgt gcc agt aaa ttt gga         1336
Leu Phe Ser Thr Ala Gly Val Glu Asp Tyr Cys Ala Ser Lys Phe Gly
                205                 210                 215 gtt gtg ggt ttt cat gaa tcc ctg agc cat gaa cta aag gct gct gaa         1384
Val Val Gly Phe His Glu Ser Leu Ser His Glu Leu Lys Ala Ala Glu
                220                 225                 230 aag gat gga att aaa aca acc ttg gtt tgc cct tat ctt gta gac act         1432
Lys Asp Gly Ile Lys Thr Thr Leu Val Cys Pro Tyr Leu Val Asp Thr
                235                 240                 245 ggc atg ttc aga ggc tgc cga atc agg aaa gaa att gag cct ttt ctg         1480
Gly Met Phe Arg Gly Cys Arg Ile Arg Lys Glu Ile Glu Pro Phe Leu
250                 255                 260 cca cct ctg aag cct gat tac tgt gtg aag cag gcc atg aag gcc atc         1528
Pro Pro Leu Lys Pro Asp Tyr Cys Val Lys Gln Ala Met Lys Ala Ile
265                 270                 275                 280 ctc act gac cag ccc atg atc tgc act ccc cgc ctc atg tac atc gtg         1576
Leu Thr Asp Gln Pro Met Ile Cys Thr Pro Arg Leu Met Tyr Ile Val
                285                 290                 295 acc ttc atg aag agc atc cta cca ttt gaa gca gtt gtg tgc atg tat         1624
```

```
Thr Phe Met Lys Ser Ile Leu Pro Phe Glu Ala Val Val Cys Met Tyr
            300                 305                 310 cgg ttc cta gga gcg gac aag tgt atg tac ccc ttt att gct caa aga    1672
Arg Phe Leu Gly Ala Asp Lys Cys Met Tyr Pro Phe Ile Ala Gln Arg
            315                 320                 325 aag caa gcc aca aac aat aat gaa gca aaa aat gga atc taa            1714
Lys Gln Ala Thr Asn Asn Asn Glu Ala Lys Asn Gly Ile
            330                 335                 340 gaatctttt  gtatggaata  ttacttctat  cagaagatga  tcaagatgtt  tcagtccagt    1774
gcacatcagc  attgctgaca  ttttatggat  tctaaacttg  tgttgtttct  tttttaaatc    1834
aactttttaa  aaaaataaag  tgtaaattaa  ccgactagag  tacttggaaa  atgtgatcag    1894
tacaagtgaa  cttaggttgt  tgccaacagg  gtccttttag  gcagaaccca  gaaaccagtc    1954
aaatctgtag  agaagcagtg  tgacatcttc  aggttaccat  tatttttaa  tgagcaggaa    2014
gtctagaaat  gataactaga  ctgtatgttt  catgtgtgtg  attttcaga  attcccagag    2074
tttactcatt  cttgttatta  aactctagcc  agttgacatc  ttcgcaattt  caaggactga    2134
tagtgctgta  ttttctcacg  ttttctaagt  ttccgttttg  caaggcctag  gtgactttt    2194
catggtgttt  gtatgtttag  ctcttttgaa  aaggaatttt  gaaatctcca  tcaactgaag    2254
taaatgatgt  ctgagtgtta  cagtaaaggt  gaccaagtct  ctttcttaaa  gtcacaatga    2314
ctaaagtatt  agttgaattt  tttttttttt  tttttgatg  gagtctcgct  ctgtcaccag    2374
gctggagtgc  agtagcacaa  tcacggctca  ctgcaatctc  tgcctcccag  tttcaagtga    2434
ttctgctgtc  tcagcctccc  aagtagctgg  gactacaggc  atgcgccacc  acgcccagct    2494
aattttgta  ttttagtag  agacgggtt  tcaccatgtt  ggtcaggatg  gtctccatct    2554
cttgacattg  tgatccacct  gcctcggcct  cccaaagtgc  tgggattaca  ggcatgagcc    2614
actgcaccca  gccttgaatt  tttaatttta  tctctgatat  acttcattaa  gtgtctggag    2674
acctaattat  cctaaaagat  catacatttt  ctacctatga  attttgctgc  atacagaaag    2734
tgcccttttc  tcaggaagtt  gctgtgtttc  atttctttgg  atggactctt  atctagaata    2794
catagcagct  ctgcaaagga  acagttttta  aaaatgggaa  cttctacatt  gaaaagtccc    2854
cattttgtg  ccaactatga  ttagtgagag  gaagaaatct  tattctatgg  catatgtatg    2914
gaagggtgta  aagattcttt  tgaaaggttt  attcacattg  tagaacagca  aatgacattt    2974
ttacagtatt  ttttgtaaa  gcaaactatt  ttgtgccttg  aatttggtat  atgtgtatta    3034
gtgaaacatt  gtaaaggtga  acttctacct  ctgtatctaa  atgtatacca  tccacttgta    3094
aatgactata  aactattatg  tgattgcttt  ttttttaga  atgtcttgtt  taaatagtgg    3154
ccaatgttta  aggctgttaa  aataagccaa  cttttactaa  ttggggagtt  ttataaatga    3214
ctgattaaat  ttaagaatt  aacttacatg  caattgtgtg  attattagtt  atcagcagtg    3274
ttgtaaggaa  aattattgtg  ttttttttta  tgatcattat  cccactttag  gtaaagaaaa    3334
atattggaat  ggaatagtgt  tgggaaacag  acattaacaa  cctagggtgc  ctgcactcaa    3394
atagccgatg  ttactgtccc  tagattagag  acttgattaa  gggcttgttt  gtaccaaaag    3454
tggggaaaca  atgccatgac  ctgtgtttta  gtttggctgc  accacagatc  aaatctgcac    3514
tgtgtctaca  tataggaaag  gtcctggtgt  gtgctaatgt  tcccaatgca  ggacttgagg    3574
aagagctctg  ttatatgttt  ccatttctct  ttatcaaaga  taaccaaacc  ttatggccct    3634
tataacaatg  gaggcactgg  ctgcctctta  attttcaatc  atggacctaa  agaagtactc    3694
tgaagggtct  caacaatgcc  aggtggggac  agatatactc  agagattatc  caggtctgcc    3754
```

```
tcccagcgag cctggagtac accagaccct cctagagaaa tctgttataa tttaacaacc    3814
cacttatcca ccttaaaact gaggaaagtc gtctttacat ctaattttat tcttgtgtgt    3874
tataacttaa acctatttct attttttgttt gttattgccc ttataagggt gtccatctcc   3934
aagttcaata aactaattca tttaactttta aaaaaaaaaa aaaaaaa                 3981

<210> SEQ ID NO 3
<211> LENGTH: 16
<212> TYPE: PRT
<213> ORGANISM: Homo sapiens

<400> SEQUENCE: 3

Lys Arg Tyr Phe Lys Leu Ser His Leu Gln Met His Ser Arg Lys His
1               5                   10                  15

<210> SEQ ID NO 4
<211> LENGTH: 22
<212> TYPE: PRT
<213> ORGANISM: Homo sapiens

<400> SEQUENCE: 4

Ala Leu Ala Glu Thr Ser Tyr Val Lys Val Leu Glu His Val Val Arg
1               5                   10                  15

Val Asn Ala Arg Val Arg
            20

<210> SEQ ID NO 5
<211> LENGTH: 15
<212> TYPE: PRT
<213> ORGANISM: Homo sapiens

<400> SEQUENCE: 5

Thr Leu Gly Glu Phe Leu Lys Leu Asp Arg Glu Arg Ala Lys Asn
1               5                   10                  15
```

METHOD FOR MODIFYING T CELL POPULATION

TECHNICAL FIELD

The present invention relates to a method for modifying a population of T cells by modulating the differentiation of immune cells, particularly T cells. In detail, the present invention relates to a compound which increases the proportion of memory T cells in a population of T cells, a method for increasing the proportion of memory T cells in a population of T cells by use of the same, and the like.

BACKGROUND ART

Immunotherapy generally refers to methods for treating diseases by activating the patient's immune system by a variety of methods, introducing immune cells activated outside the patient's body into the patient's body, and the like. As immunotherapy, various methods such as immune cell therapy, peptide vaccine therapy, cytokine therapy, and antibody therapy have been so far developed.

In recent years, it has been found out that induction of tumor-specific cytotoxic T cells (CTL) and activation of helper T cells can be achieved by stimulating immune cells (particularly antigen-presenting cells and T cells) using partial peptides (WT1 peptides) derived from the oncogene product WT1 (Patent Literatures 1 to 4 and Non-Patent Literature 1), and researches for practical use thereof as cancer immunotherapy by WT1 peptide vaccine are in progress.

However, few immunotherapies have been effective in clinical trials like the WT1 peptide vaccine. In addition, there is a case in which immunotherapy is not sufficiently effective depending on the immune status (immune suppression, differentiation stage and activity of immune cells) in the patient, and thus development of a method for enhancing the effect of immunotherapy is desirable.

The present inventors have found out that the proportion of memory T cells in a T cell population can be increased and the immune response in a subject can be enhanced by modulating the retinoid metabolic pathway or retinoic acid signaling system (Patent Literature 5).

CITATION LIST

Patent Literature

Patent Literature 1: WO 2003/106682 A
Patent Literature 2: WO 2005/095598 A
Patent Literature 3: WO 2007/097358 A
Patent Literature 4: WO 2012/046730 A
Patent Literature 5: WO 2016/104486 A

Non-Patent Literature

Non-Patent Literature 1: Oka Y et al., Immunogenetics. 2000 February; 51(2):99-107

DISCLOSURE OF INVENTION

Problem to be Solved by the Invention

An object of the present invention is to search for compounds which can increase the proportion of memory T cells in a T cell population and enhance the immune response in a subject by modulating the retinoid metabolic pathway or retinoic acid signaling system.

Means for Solving the Problem

The present inventors have searched for compounds which can increase the proportion of memory T cells in a T cell population and enhance the immune response in a subject by modulating the retinoid metabolic pathway or retinoic acid signaling system, as a result, found out that the proportion of memory T cells in a T cell population can be increased and the immune response in a subject can be enhanced as a compound represented by a formula (I) or a That is, the present invention provides the following:

(1) A compound represented by a formula (I) or a pharmaceutically acceptable salt or hydrate of the compound:

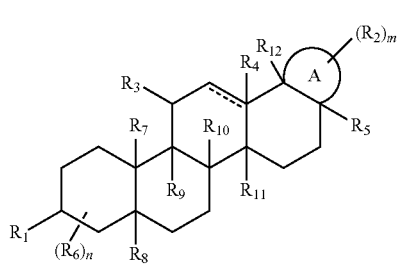

[Chem. 1]

[wherein, A represents a 5- or 6-membered ring,
⁓⁓⁓ represents a single bond or a double bond,
m represents an integer from 0 to 2,
n represents an integer from 0 to 2,
$R_1$ represents —$NH_2$ which may be substituted with a $C_{1-6}$ alkyl group, —OH, =O, =NOH, —NHC(O)—$R_{13}$, —NHC(O)NH—$R_{14}$, or —OC(O)—$R_{15}$,
$R_2$ represents a —$C_{1-6}$ alkyl group, a $C_{2-6}$ alkenyl group which may be substituted with a —$C_{1-6}$ alkyl group, —C(O)OH which may be substituted with a —$C_{1-6}$ alkyl group, —NHC(O)OH which may be substituted with a —$C_{1-6}$ alkyl group, or —C(O)$NH_2$ which may be substituted with a —$C_{1-6}$ alkyl group,
$R_3$ represents —H, =O, or a —$C_{1-6}$ alkyl group,
$R_4$ represents absence, —H, or a —$C_{1-6}$ alkyl group,
$R_5$ represents a —$C_{1-6}$ alkyl group which may be substituted with OH or —C(O)OH which may be substituted with a —$C_{1-6}$ alkyl group,
$R_6$ represents —H or a —$C_{1-6}$ alkyl group,
$R_7$ represents —H or a —$C_{1-6}$ alkyl group,
$R_8$ represents —H or a —$C_{1-6}$ alkyl group,
$R_9$ represents —H or a —$C_{1-6}$ alkyl group,
$R_{10}$ represents —H or a —$C_{1-6}$ alkyl group,
$R_{11}$ represents —H or a —$C_{1-6}$ alkyl group,
$R_{12}$ represents —H or a —$C_{1-6}$ alkyl group,
$R_{13}$ represents a $C_{1-6}$ alkyl group, a phenyl group which may be substituted with a carboxy group which may be substituted with a $C_{1-6}$ alkyl group, a $C_{2-6}$ alkenyl group which may be substituted with a carboxy group, or a morpholino group,
$R_{14}$ represents a phenyl group which may be substituted with a carboxy group which may be substituted with a $C_{1-6}$ alkyl group, a $C_{1-6}$ alkyl group which may be substituted with a carboxy group which may be substituted with a $C_{1-6}$ alkyl group, or a $C_{1-6}$ alkyl group which may be substituted with a carboxy group and/or a phenyl group which may be substituted with a $C_{1-6}$ alkyl group, and $R_{15}$ represents a pyrrolidino group which may be substituted with a carboxy group which may be substituted with a $C_{1-6}$ alkyl group, a piperidino group which may be substituted with a carboxy group which may be substituted with a $C_{1-6}$ alkyl group, or a phenyl group which may be substituted with a carboxy group which may be substituted with a $C_{1-6}$ alkyl group].

(2) The compound according to (1) or a pharmaceutically acceptable salt or hydrate of the compound, wherein ring A represents a 6-membered ring, ----- represents a single bond or a double bond, m represents 2, n represents 2, $R_1$ represents $—NH_2$ which may be substituted with a methyl group, —OH, =O, =NOH, —NHC(O)—$R_{13}$, —NHC(O)NH—$R_{14}$, or —OC(O)—$R_{15}$, $R_2$ represents a -methyl group, —C(-methyl group)=$CH_2$, —C(O)OH which may be substituted with a methyl group, —NHC(O)OH which may be substituted with a methyl group, or —C(O)$NH_2$, $R_3$ represents =O, $R_4$ represents absence, $R_5$ represents a methyl group, $R_6$ represents a methyl group, $R_7$ represents a methyl group, $R_8$ represents —H, $R_9$ represents —H, $R_{10}$ represents a methyl group, $R_{11}$ represents a methyl group, $R_{12}$ represents —H, $R_{13}$ represents a methyl group, a phenyl group which may be substituted with a carboxy group which may be substituted with a methyl group, an ethylene group which may be substituted with a carboxy group, or a morpholino group, $R_{14}$ represents a phenyl group which may be substituted with a carboxy group which may be substituted with a methyl group, a methyl group which may be substituted with a carboxy group which may be substituted with an ethyl group, or an ethyl group which may be substituted with a carboxy group and a phenyl group which may be substituted with a methyl group, and $R_{15}$ represents a pyrrolidino group which may be substituted with a carboxy group which may be substituted with a methyl group, a piperidino group which may be substituted with a carboxy group which may be substituted with a methyl group, or a phenyl group which may be substituted with a carboxy group.

(3) A compound selected from the group consisting of (2S,4aS,6aS,6bR,8aR,12aS,12bR,14bS)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 1 (RDHI012)), (2S,4aS,6aS,6bR,8aR,12aS,12bR,14bR)-methyl10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 2 (RDHI013)), 2-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylcarbamoyl)benzoic acid (Compound No. 3 (RDHI014)), 2-((4aR,6aR,6bS,8aS,11S,12aR,14aR,14bS)-11-(methoxycarbonyl)-4,4,6a,6b,8a,11,12a,14-octamethyl-14-oxo-1,2,3,4,4a,5,6,6a,6b,7,8,8a,9,10,11,12,12a,14,14a,14b-icosahydropicen-3-ylcarbamoyl)benzoic acid (Compound No. 4 (RDHI015)), (Z)-4-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylamino)-4-oxobut-2-enoic acid (Compound No. 5 (RDHI016)), (Z)-4-((4aR,6aR,6bS,8aS,11S,12aR,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylamino)-4-oxobut-2-enoic acid (Compound No. 6 (RDHI017)), 1-(3S,4aR,6aR,6bS,8aS,11S,12aS,14aR,14bS)-11-(methoxycarbonyl)-4,4,6a,6b8a,11,14b-heptamethyl-14-oxo-1,2,3,4,4a,5,6,6a,6b,7,8,8a,9,10,11,12,12a,14,14a,14b-icosahydropicen-3-yl 2-methyl pyrrolidine-1,2-dicarboxylate (Compound No. 7 (RDHI021)), 1-(3S,4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl2-methyl piperidine-1,2-dicarboxylate (Compound No. 8 (RDHI022)), (2S,4aS,6aS,6bR,8aR,12aS,12bR,14bS)-methyl 10-(3-(2-(methoxycarbonyl)phenyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 9 (RDHI023)), (2S,4aS,6aS,6bR,8aR,12aS,12bR,14bS)-methyl 10-(3-(2-ethoxy-2-oxoethyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 10 (RDHI024)), (2S,4aS,6aS,6bR,8aR,12aS,12bR,14bS)-methyl 10-(3-((S)-1-methoxy-1-oxo-3-phenylpropan-2-yl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 11 (RDHI025)), 2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)benzoic acid (Compound No. 12 (RDHI026)), 2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)acetic acid (Compound No. 13 (RDHI027)), (2S)-2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)-3-phenyl propanoic acid (Compound No. 14 (RDHI028)), 2-(((3S,4aR,6aR,6bS,8aS,11S,12aS,14aR,14bS)-11-(methoxycarbonylamino)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yloxy)carbonyl)benzoic acid (Compound No. 15 (RDHI031)), (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 16 (RDHI032)), (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 17 (RDHI033)), and (2S,4aS,6aS,6bR,8aR,12aS,12bR,14bR)-10-benzamide-2,
4a,6a,6b,9,9,12a-heptamethyl-13-oxo-1,2,3,4,4a,5,6,6a,
6b,7,8,8a,9,10,11,12,12a,12b,13,14b-icosahydropicene-
2-carboxamide (Compound No. 18 (RDHI034)),
or a pharmaceutically acceptable salt or hydrate of the compound.

(4) A compound selected from the group consisting of
(2S,4aS,6aS,6bR,8aR,12aS,12bR,14bS)-methyl 10-amino-
2,4a,6a,6b,9,9,12a-heptamethyl-13-oxo-1,2,3,4,4a,5,6,6a,
6b,7,8,8a,9,10,11,12,12a,12b,13,14b-icosahydropicene-
2-carboxylate (Compound No. 1 (RDHI-012)),
(2S,4aS,6aS,6bR,8aR,12aS,12bR,14bR)-methyl 10-amino-
2,4a,6a,6b,9,9,12a-heptamethyl-13-oxo-1,2,3,4,4a,5,6,6a,
6b,7,8,8a,9,10,11,12,12a,12b,13,14b-icosahydropicene-
2-carboxylate (Compound. No. 2 (RDHI-013)),
(Z)-4-((4aR,6aR,6bS,8aS,11S,12aS,14aR,14bS)-11-
(methoxycarbonyl)-4,4,6a,6b,8a,11,14b-heptamethyl-14-
oxo-1,2,3,4,4a,5,6,6a,6b,7,8,8a,9,10,11,12,12a,14,14a,
14b-icosahydropicen-3-ylamino)-4-oxobut-2-enoic acid
(Compound No. 5 (RDHI-016)),
(2S,4aS,6aS,6bR,8aR,12aS,12bR,14bS)-methyl 104342-
(methoxycarbonyl)phenyl)ureido)-2,4a,6a,6b,9,9,12a-
heptamethyl-13-oxo-1,2,3,4,4a,5,6,6a,6b,7,8,8a,9,10,11,
12,12a,12b,13,14b-icosahydropicene-2-carboxylate
(Compound No. 9 (RDHI-023)),
(2S,4aS,6aS,6bR,8aR,12aS,12bR,14bS)-methyl 10-(3-(2-
ethoxy-2-oxoethyl)ureido)-2,4a,6a,6b,9,9,12a-heptam-
ethyl-13-oxo-1,2,3,4,4a,5,6,6a,6b,7,8,8a,9,10,11,12,12a,
12b,13,14b-icosahydropicene-2-carboxylate (Compound
No. 10 (RDHI-024)),
(2S)-2-(3-((4aR,6aR,6bS,8aS,11S,12aS,14aR,14bS)-11-
(methoxycarbonyl)-4,4,6a,6b,8a,11,14b-heptamethyl-14-
oxo-1,2,3,4,4a,5,6,6a,6b,7,8,8a,9,10,11,12,12a,14,14a,
14b-icosahydropicen-3-yl)ureido)-3-phenyl propanoic
acid (Compound No. 14 (RDHI-028)),
(2S,4aS,6aS,6bR,8aR,12aS,12bR,14bR)-10-amino-2,4a,6a,
6b,9,9,12a-heptamethyl-13-oxo-1,2,3,4,4a,5,6,6a,6b,7,8,
8a,9,10,11,12,12a,12b,13,14b-icosahydropicene-2-car-
boxamide (Compound No. 16 (RDHI-032)),
(2S,4aS,6aS,6bR,8aR,12aS,12bR,14bR)-10-acetamido-2,
4a,6a,6b,9,9,12a-heptamethyl-13-oxo-1,2,3,4,4a,5,6,6a,
6b,7,8,8a,9,10,11,12,12a,12b,13,14b-icosahydropicene-
2-carboxamide (Compound No. 17 (RDHI-033)), and
(2S,4aS,6aS,6bR,8aR,12aS,12bR,14bR)-10-benzamide-2,
4a,6a,6b,9,9,12a-heptamethyl-13-oxo-1,2,3,4,4a,5,6,6a,
6b,7,8,8a,9,10,11,12,12a,12b,13,14b-icosahydropicene-
2-carboxamide (Compound No. 18 (RDHI-034)),
or a pharmaceutically acceptable salt or hydrate of the compound.

(5) An inhibitor of a retinoid metabolic pathway, comprising the compound according to any one of (1) to (4) or a pharmaceutically acceptable salt or hydrate of the compound.

(6) An agent for increasing a proportion of a memory T cell, comprising the compound according to any one of (1) to (4) or a pharmaceutically acceptable salt or hydrate of the compound.

(7) A preventive and/or therapeutic agent for cancer or an infectious disease, comprising the compound according to any one of (1) to (4) or a pharmaceutically acceptable salt or hydrate of the compound.

(8) An adjuvant for cancer immunotherapy, comprising the compound according to any one of (1) to (4) or a pharmaceutically acceptable salt or hydrate of the compound.

(9) An immunity enhancer comprising the compound according to any one of (1) to (4) or a pharmaceutically acceptable salt or hydrate of the compound.

(10) A method for producing a T cell population having an increased proportion of a memory T cell, comprising adding the compound according to any one of (1) to (4) or a pharmaceutically acceptable salt or hydrate of the compound to the T cell population.

Furthermore, the present invention provides the following.

(11) Use of the compound according to any one of (1) to (4) or a pharmaceutically acceptable salt or hydrate of the compound in preparation of an inhibitor of a retinoid metabolic pathway.

(12) Use of the compound according to any one of (1) to (4) or a pharmaceutically acceptable salt or hydrate of the compound in preparation of an agent for increasing a proportion of a memory T cell.

(13) Use of the compound according to any one of (11 to (4) or a pharmaceutically acceptable salt or hydrate of the compound in preparation of a preventive and/or therapeutic agent for cancer or an infectious disease.

(14) Use of the compound according to any one of (1) to (4) or a pharmaceutically acceptable salt or hydrate of the compound in preparation of an adjuvant for cancer immunotherapy.

(15) Use of the compound according to any one of (1) to (4) or a pharmaceutically acceptable salt or hydrate of the compound in preparation of an immunity enhancer.

Furthermore, the present invention provides the following.

(16) Use of the compound according to any one of (1) to (4) or a pharmaceutically acceptable salt or hydrate of the compound for inhibiting a retinoid metabolic pathway.

(17) Use of the compound according to any one of (1) to (4) or a pharmaceutically acceptable salt or hydrate of the compound for increasing a proportion of a memory T cell.

(18) Use of the compound according to any one of (1) to (4) or a pharmaceutically acceptable salt or hydrate of the compound for preventing and/or treating cancer or an infectious disease.

(19) Use of the compound according to any one of (1) to (4) or a pharmaceutically acceptable salt or hydrate of the compound for assisting cancer immunotherapy.

(20) Use of the compound according to any one of (1) to (4) or a pharmaceutically acceptable salt or hydrate of the compound for enhancing immunity.

Furthermore, the present invention provides the following.

(21) A method for inhibiting a retinoid metabolic pathway in a subject in need of inhibition of a retinoid metabolic pathway, comprising administering the compound according to any one of (1) to (4) or a pharmaceutically acceptable salt or hydrate of the compound to the subject.

(22) A method for increasing a proportion of a memory T cell in a subject in need of an increase in a proportion of a memory T cell, comprising administering the compound according to any one of (1) to (4) or a pharmaceutically acceptable salt or hydrate of the compound to the subject.

(23) A method for preventing and/or treating cancer or an infectious disease in a subject in need of prevention and/or treatment of cancer or an infectious disease, comprising administering the compound according to any one of (1) to (4) or a pharmaceutically acceptable salt or hydrate of the compound to the subject.

(24) A method for assisting cancer immunotherapy in a subject in need of assistance of cancer immunotherapy, comprising administering the compound according to any one of (1) to (4) or a pharmaceutically acceptable salt or hydrate of the compound to the subject.

(25) A method for enhancing immunity in a subject in need of immunity enhancement, comprising administering the compound according to any one of (1) to (4) or a pharmaceutically acceptable salt or hydrate of the compound to the subject.

Furthermore, the present invention provides the following.

(26) A kit for inhibiting a retinoid metabolic pathway, comprising the compound according to any one of (1) to (4) or a pharmaceutically acceptable salt or hydrate of the compound.

(27) A kit for increasing a proportion of a memory T cell, comprising the compound according to any one of (1) to (4) or a pharmaceutically acceptable salt or hydrate of the compound.

(28) A kit for preventing and/or treating cancer or an infectious disease, comprising the compound according to any one of (1) to (4) or a pharmaceutically acceptable salt or hydrate of the compound.

(29) A kit for cancer immunotherapy, comprising the compound according to any one of (1) to (4) or a pharmaceutically acceptable salt or hydrate of the compound.

(30) A kit for enhancing immunity, comprising the compound according to any one of (1) to (4) or a pharmaceutically acceptable salt or hydrate of the compound.

Effect of the Invention

Compounds found out in the present invention or a pharmaceutically acceptable salt or hydrate thereof can enhance the immune response to antigens in a subject through an increase in the proportion of memory T cells in a T cell population. Hence, the memory T cell proportion increasing method, the preventive and/or therapeutic agent for cancer or infectious diseases, the cancer immunotherapy adjuvant, the immunity enhancer, the T cell population producing method, the T cell population created by the method and the like of the present invention can be used for the prevention/treatment of various diseases including cancer and infectious diseases. In addition, the effect of the immunotherapy can be enhanced by combining these with immunotherapy for various diseases including cancer and infectious diseases.

MODE FOR CARRYING OUT THE INVENTION

Figure 1:
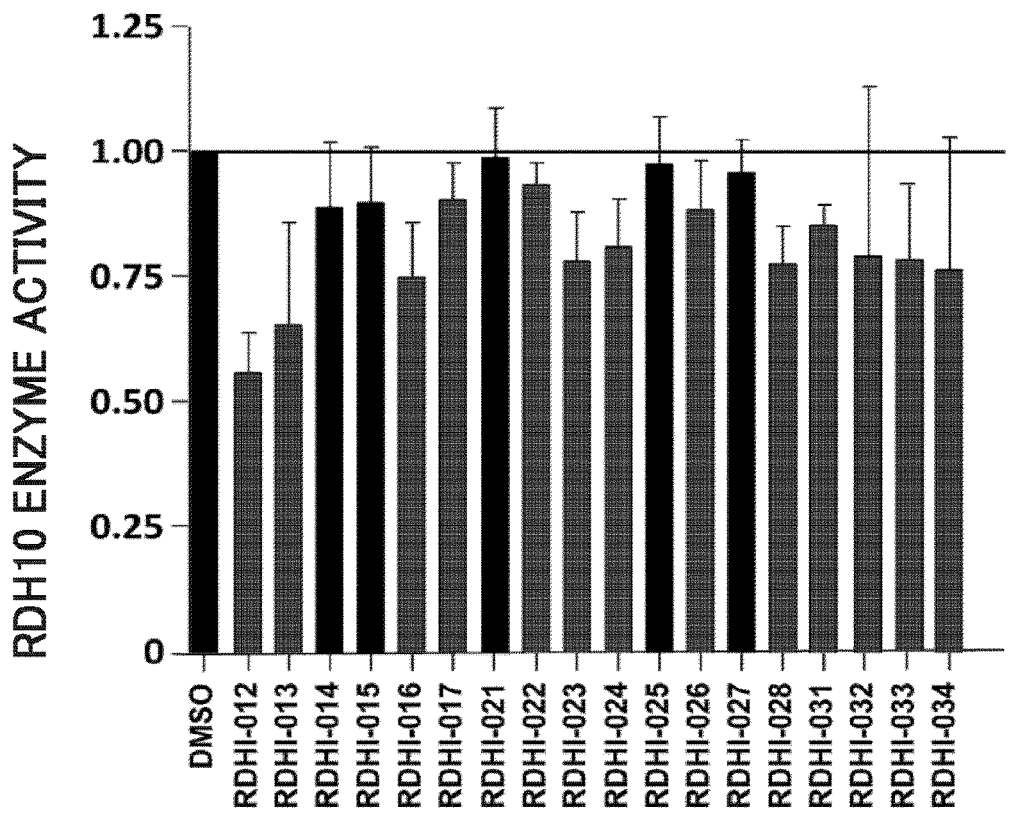
FIG. 1 is a graph illustrating an effect of inhibiting RDH10 enzyme activity by a compound of the present invention. The compound is denoted by the applicant's reference number (RDHI-No.).

T cells differentiate from naive T cells in an undifferentiated state into subsets of T cells having various functions. Among differentiated T cells, those that play a major role in the immune response are CD4 positive T cells (helper T cells) and CD8 positive T cells (killer T cells). Both the CD4 positive T cells and CD8 positive T cells can be classified into memory cells (central memory cells and effector memory cells) and effector cells (effector cells and terminal effector cells) depending on the stage of differentiation. Incidentally, in the present specification, positive for CD antigen expression is denoted by a symbol of "+" and negative is denoted by a symbol of "−". For example, CD4 positive T cells are denoted by CD4$^+$T cells.

These T cell subsets can be determined by identifying surface antigens expressed by cells, cytokines and interferons produced, and the like. For example, CD4$^+$T cells and CD$^+$T cells can be classified as any of central memory cells (CD127$^+$, CD62L$^+$), effector memory cells (CD127$^+$, CD62L$^-$), effector cells (CD127, CD62L$^+$), or terminal effector cells (CD127$^-$, CD62L$^-$) depending on the expression of surface antigens CD127 and CD62L. Stimulated T cells differentiate into central memory cells, effector memory cells, effector cells, and terminal effector cells in this order. Among these cells, central memory cells have the highest proliferative capacity and the greatest IL-2 production amount. As differentiation progresses toward terminal effector cells, IL-2 production amount decreases, IFN-γ production amount increases, and apoptosis is likely to occur. Features of memory T cells include the fact that memory T cells hardly undergo apoptosis and the fact that memory T cells have strong proliferative capacity. Consequently, an increase in the proportion of memory T cells in a T cell population according to the method of the present invention contributes to the achievement of stronger immunity.

In the present invention, the proportion of memory T cells is increased using a compound which inhibits the retinoid metabolic pathway. In detail, the proportion of memory T cells, particularly central memory T cells in a T cell population is increased by inhibiting the retinoid metabolic pathway. In the present specification, inhibition of the retinoid metabolic pathway refers to inhibition of any reaction in the metabolic pathway in which retinoic acid is produced from vitamin A (retinoid) such as retinol or β-carotene, or provitamin A (retinoid precursor). In an aspect of the present invention, the inhibitory substance of retinoid metabolic pathway is one that inhibits any one or more of a reaction to convert retinol to retinal, a reaction to convert retinal to retinoic acid, a reaction to convert β-carotene to retinal, a reaction to convert β-carotene to β-apocarotenal, or a reaction to convert β-apocarotenal to retinal and retinoic acid.

An inhibitory substance of retinoid metabolic pathway is one that inhibits the expression or action of an enzyme (hereinafter also referred to as "retinoid metabolic enzyme") which catalyzes any reaction in the retinoid metabolic pathway, for example, retinol dehydrogenase, retinal oxidase, retinal dehydrogenase, (3-carotene-15,15'-monooxygenase 1 (BCMO1), or β-carotene oxygenase 2 (BCO2). In a preferred aspect, the inhibitory substance of retinoid metabolic pathway is an inhibitory substance of retinol dehydrogenase and more preferably an inhibitory substance of retinol dehydrogenase 10 (the sequence of the DNA encoding the enzyme is denoted as SEQ ID NO: 2) consisting of the amino acid sequence of SEQ ID NO: 1 or a homologue thereof. Here, the homologue of retinol dehydrogenase 10 refers to a protein consisting of an amino acid sequence having 80% or more, 85% or more, 90% or more, 95% or more, 98% or more, or 99% or more sequence identity with the amino acid sequence of SEQ ID NO: 1 or a protein consisting of an amino acid sequence in which one or several amino acids, for example, 1, 2, 3, 4, 5, 6, 7, 8, or 9 amino acids are substituted, deleted, inserted and/or added in the amino acid, sequence of SEQ ID NO: 1.

In the present invention, the inhibitory substance of retinoid metabolic pathway is a compound represented by the following formula (I) and a pharmaceutically acceptable salt and solvate thereof. The compound represented by the formula (I) and a pharmaceutically acceptable salt and solvate thereof may be used in combination with an antibody which binds to a retinoid metabolism enzyme or an antigen-binding fragment thereof (for example, Fab, F(ab')$_2$, or the like) or ScFv or the like, a molecule which suppresses the expression of a gene encoding a retinoid metabolism enzyme (for example, siRNA, shRNA, miRNA, stRNA, antisense RNA, or the like), or a retinoic acid signaling system inhibitor or the like.

In the present invention, the proportion of memory T cells is increased by adding a compound which inhibits the retinoid metabolic pathway to a T cell population. Such addition may be performed in vitro or in vivo. Examples of in vitro addition may include addition of the modulator to a medium in which the T cell population is cultured. Examples of in vivo addition may include injection of the modulator into the subject's body.

The inhibitory substance of retinoid metabolic pathway in the present invention is a compound which inhibits the action of retinol dehydrogenase and preferably a compound (hereinafter also referred to as "RDH10 inhibitor") which inhibits the action of retinol dehydrogenase 10 (SEQ ID NO: 1). In an aspect, the RDH10 inhibitor is a compound having a structure represented by the following formula (I), a compound which inhibits the action of retinol dehydrogenase and preferably a compound (hereinafter, also referred to as "RDH10 inhibitor") which inhibits the action of retinol dehydrogenase 10 (SEQ ID NO: 1). The RDH10 inhibitor may be a compound having a structure represented by the following formula (I) or a salt thereof.

Therefore, in an aspect, the present invention provides a compound represented by a formula (I) and a pharmaceutically acceptable salt and solvate thereof:

[Chem. 2]

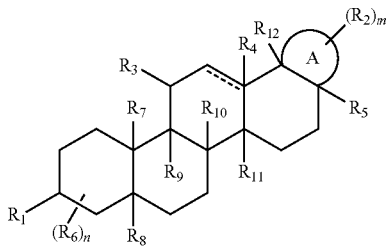

[wherein, A represents a 5- or 6-membered ring,

------ represents a single bond or a double bond, m represents an integer from 0 to 2, n represents an integer from 0 to 2, $R_1$ represents —NH$_2$ which may be substituted with a $C_{1-6}$ alkyl group, —OH, =O, —NOH, —NHC(O)—$R_{13}$, —NHC(O) NH—$R_{14}$, or —OC(O)—$R_{15}$, $R_2$ represents a —$C_{1-6}$ alkyl group, a —$C_{2-6}$ alkenyl group which may be substituted with a —$C_{1-6}$ alkyl group, —C(O)OH which may be substituted with a —$C_{1-6}$ alkyl group, —NHC(O)OH which may be substituted with a —$C_{1-6}$ alkyl group, or —C(O)NH$_2$ which may be substituted with a —$C_{1-6}$ alkyl group, $R_3$ represents —H, =O, or a —$C_{1-6}$ alkyl group, $R_4$ represents absence, —H, or a —$C_{1-6}$ alkyl group, $R_5$ represents a —$C_{1-6}$ alkyl group which may be substituted with OH or —C(O)OH which may be substituted with a —$C_{1-6}$ alkyl group, $R_6$ represents —H or a —$C_{1-6}$ alkyl group, $R_7$ represents —H or a —$C_{1-6}$ alkyl group, $R_8$ represents —H or a —$C_{1-6}$ alkyl group, $R_9$ represents —H or a —$C_{1-6}$ alkyl group, $R_{10}$ represents —H or a —$C_{1-6}$ alkyl group, $R_{11}$ represents —H or a —$C_{1-6}$ alkyl group, $R_{12}$ represents —H or a —$C_{1-6}$ alkyl group, $R_{13}$ represents a $C_{1-6}$ alkyl group, a phenyl group which may be substituted with a carboxy group which may be substituted with a alkyl group, a $C_{2-6}$ alkenyl group which may be substituted with a carboxy group, or a morpholino group, $R_{14}$ represents a phenyl group which may be substituted with a carboxy group which may be substituted with a $C_{1-6}$ alkyl group, a $C_{1-6}$ alkyl group which may be substituted with a carboxy group which may be substituted with a $C_{1-6}$ alkyl group, or a $C_{1-6}$ alkyl group which may be substituted with a carboxy group and/or a phenyl group which may be substituted with a $C_{1-6}$ alkyl group, and $R_{15}$ represents a pyrrolidino group which may be substituted with a carboxy group which may be substituted with a $C_{1-6}$ alkyl group, a piperidino group which may be substituted with a carboxy group which may be substituted with a $C_{1-5}$ alkyl group, or a phenyl group which may be substituted with a carboxy group which may be substituted with a $C_{1-6}$ alkyl group].

Among the compounds represented by the formula (I), those are preferable in which ring A represents a 6-membered ring, ------ represents a single bond or a double bond, m represents 2, n represents 2, $R_1$ represents —NH$_2$ which may be substituted with a methyl group, —OH, =O, =NOH, —NHC(O)—$R_{13}$, —NHC(O)NH—$R_{14}$, or —OC(O)—$R_{15}$, $R_2$ represents a -methyl group, —C(-methyl group)=$CH_2$, —C(O)OH which may be substituted with a methyl group, NHC(O)OH which may be substituted with a methyl group, or —C(O)$NH_2$, $R_3$ represents =O, $R_4$ represents absence, $R_5$ represents a methyl group, $R_6$ represents a methyl group, $R_7$ represents a methyl group, $R_8$ represents —H, $R_9$ represents —H, $R_{10}$ represents a methyl group, $R_{11}$ represents a methyl group, $R_{12}$ represents —H, $R_{13}$ represents a methyl group, a phenyl group which may be substituted with a carboxy group which may be substituted with a methyl group, an ethylene group which may be substituted with a carboxy group, or a morpholino group, $R_{14}$ represents a phenyl group which may be substituted with a carboxy group which may be substituted with a methyl group, a methyl group which may be substituted with a carboxy group which may be substituted with an ethyl group, or an ethyl group which may be substituted with a carboxy group and a phenyl group which may be substituted with a methyl group, and $R_{15}$ represents a pyrrolidino group which may be substituted with a carboxy group which may be substituted with a methyl group, a piperidino group which may be substituted with a carboxy group which may be substituted with a methyl group, or a phenyl group which may be substituted with a carboxy group.

The compounds represented by the formula (I) encompass all kinds of isomers including structural isomers and stereoisomers unless otherwise specified. The compound represented by a formula (I) and the pharmaceutically acceptable salt and solvate thereof can increase the proportion of memory T cells in the T cell population by inhibiting the retinoid metabolic pathway.

The compounds represented by the formula (I) can be synthesized by known methods. For example, the compounds of the present invention can be synthesized by known methods using 18α- or 18β-glycyrrhetinic acid as a starting material.

Salts of the compounds of the present invention are also encompassed in the present invention. The salts can be manufactured in accordance with a conventional method using the compounds which are represented by the formula (I) and provided by the present invention.

Specifically, in a case in which the compound represented by the formula (I) has a basic group such as an amino group or a pyridyl group, the compound can be converted to an acid addition salt by being treated with an acid.

Examples of the acid addition salt of the compound of the present invention may include hydrohalic acid salts such as hydrochloride, hydrofluoride, hydrobromide, and hydroiodide; inorganic acid salts such as nitrates, perchlorates, sulfates, phosphates, and carbonates; lower alkyl sulfonates such as methanesulfonates, trifluoromethanesulfonates, and ethanesulfonates; aryl sulfonates such as benzene sulfonates and p-toluene sulfonates; organic acid salts such as fumarates, succinates, citrates, tartrates, oxalates, and maleates; and acid addition salts with organic acids such as amino acids such as glutamates and aspartates, but are not limited thereto.

In addition, in a case in which the compound of the present invention has an acidic group such as a carboxyl group, the compound can be converted to a base addition salt by being treated with a base.

Examples of such a base addition salt may include salts of alkali metals such as sodium and potassium; salts of alkaline earth metals such as calcium and magnesium; ammonium salts; and salts with organic bases such as guanidine, triethylamine, dicyclohexylamine, but are not limited thereto.

Furthermore, the compound of the present invention may exist as any solvates of the free compound or salts thereof. Examples of such solvates of the compound of the present invention may include hydrates, but are not limited thereto.

In the present specification, the phrase "compound of the present invention" is intended to encompass the compounds represented by the formula (I) and salts and solvates thereof unless otherwise specified.

The compound of the present invention may exist as possible isomers. The compound may exist as, for example, geometric (cis or trans) isomers, optical isomers (enantiomers, antipodes), or racemates or as mixtures thereof. The possible isomers or mixtures thereof described above are within the scope of the present invention.

In the present specification, the "$C_{1-6}$ alkyl group" means a linear or branched alkyl group having one, two, three, four, five, or six carbon atoms, and examples thereof may include a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-2-methylpropyl group, but are not limited thereto.

Other terms in the present specification shall have the meanings commonly used in the art.

Specific examples of preferred compounds represented by the formula (I) of the present invention may include the compounds presented in Table 1 and pharmaceutically acceptable salts and solvates thereof, but are not limited thereto. The IUPAC names of the compounds in Table 1 are presented in Table 2.

TABLE 1-1

| Compound No. | Applicant's reference number (RDHI-No.) and denotation of α and β at 18th position | Molecular formula and molecular weight | Structural formula |
|---|---|---|---|
| 1 | RDHI-012<br>18α | $C_{30}H_{51}NO_3$<br>Mol. Wt.: 473.74 | |
| 2 | RDHI-013<br>18β | $C_{30}H_{51}NO_3$<br>Mol. Wt.: 473.74 | |
| 3 | RDHI-014<br>18α | $C_{39}H_{53}NO_6$<br>Mol. Wt.: 631.85 | |
| 4 | RDHI-015<br>18β | $C_{39}H_{53}NO_6$<br>Mol. Wt.: 631.85 | |

TABLE 1-1-continued

| Compound No. | Applicant's reference number (RDHI-No.) and denotation of α and β at 18th position | Molecular formula and molecular weight | Structural formula |
|---|---|---|---|
| 5 | RDHI-016<br>18α | $C_{35}H_{51}NO_6$<br>Mol. Wt.: 581.79 | |
| 6 | RDHI-017<br>18β | $C_{35}H_{51}NO_6$<br>Mol. Wt.: 581.79 | |
| 7 | RDHI-021<br>18α | $C_{38}H_{57}NO_7$<br>Mol. Wt.: 639.87 | |
| 8 | RDHI-022<br>18α | $C_{39}H_{59}NO_7$<br>Mol. Wt.: 653.90 | |

TABLE 1-1-continued

| Compound No. | Applicant's reference number (RDHI-No.) and denotation of α and β at 18th position | Molecular formula and molecular weight | Structural formula |
| --- | --- | --- | --- |
| 9 | RDHI-023<br>18α | $C_{40}H_{56}N_2O_6$<br>Mol Wt: 660.90 | |
| 10 | RDHI-024<br>18α | $C_{36}H_{56}N_2O_6$<br>Mol Wt: 612.85 | |
| 11 | RDHI-025<br>18α | $C_{42}H_{60}N_2O_6$<br>Mol Wt: 688.95 | |

TABLE 1-1-continued

| Compound No. | Applicant's reference number (RDHI-No.) and denotation of α and β at 18th position | Molecular formula and molecular weight | Structural formula |
|---|---|---|---|
| 12 | RDHI-026 18α | $C_{39}H_{54}N_2O_6$ Mol Wt: 646.87 | |
| 13 | RDHI-027 18α | $C_{34}H_{52}N_2O_6$ Mol Wt:: 584.80 | |
| 14 | RDHI-028 18α | $C_{41}H_{58}N_2O_6$ Mol Wt:: 674.92 | |

TABLE 1-1-continued
| Compound No. | Applicant's reference number (RDHI-No.) and denotation of α and β at 18th position | Molecular formula and molecular weight | Structural formula |
| --- | --- | --- | --- |
| 15 | RDHI-031<br>18α | $C_{39}H_{53}NO_7$<br>Mol Wt: 647.85 | 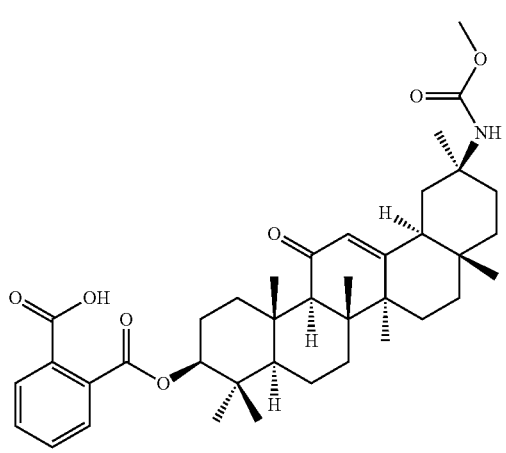 |
| 16 | RDHI-032<br>18β | $C_{30}H_{48}N_2O_2$<br>Mol. Wt.: 468.73 | 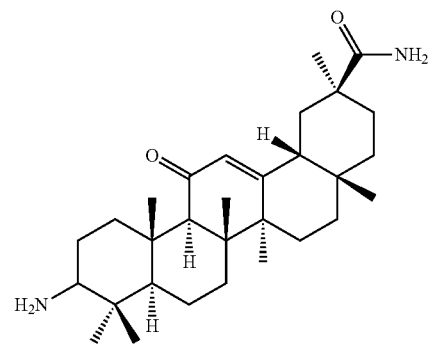 |
| 17 | RDHI-033<br>18β | $C_{32}H_{50}N_2O_3$<br>Mol. Wt.: 510.76 | 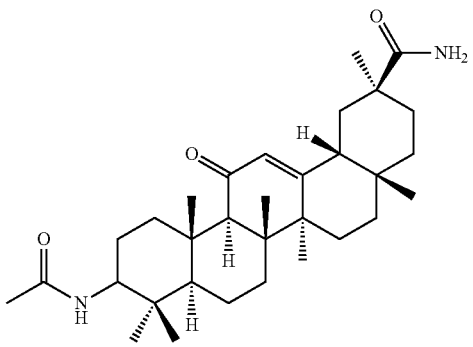 |

TABLE 1-1-continued

| Compound No. | Applicant's reference number (RDHI-No.) and denotation of α and β at 18th position | Molecular formula and molecular weight | Structural formula |
| --- | --- | --- | --- |
| 18 | RDHI-034<br>18β | $C_{37}H_{52}N_2O_3$<br>Mol. Wt.: 572.83 | |
| 19 | RDHI-035<br>18α | $C_{30}H_{48}N_2O_2$<br>Mol. Wt.: 468.73 | |
| Intermediate of 19 | RDHI-036<br>18α | $C_{30}H_{48}N_2O_2$<br>Mol. Wt.: 468.37, | |
| Intermediate of 19 | RDHI-037<br>18α | $C_{30}H_{45}NO_3$<br>Mol. Wt.: 467.34 | |

TABLE 1-1-continued

| Compound No. | Applicant's reference number (RDHI-No.) and denotation of α and β at 18th position | Molecular formula and molecular weight | Structural formula |
| --- | --- | --- | --- |
| Intermediate of 19 | RDHI-038<br>18α | $C_{30}H_{46}N_2O_3$<br>Mol. Wt.: 482.35 | |
| 20 | RDHI-039<br>18α | $C_{30}H_{47}NO_3$<br>Mol. Wt.: 469.71 | |
| 21 | RDHI-040<br>18β | $C_{30}H_{47}NO_3$<br>Mol. Wt.: 469.7 | |
| 22 | RDHI-041<br>18α | $C_{36}H_{56}N_2O_5$<br>Mol. Wt.: 596.85 | |

TABLE 1-1-continued

| Compound No. | Applicant's reference number (RDHI-No.) and denotation of α and β at 18th position | Molecular formula and molecular weight | Structural formula |
| --- | --- | --- | --- |
| 23 | RDHI-042<br>18β | $C_{36}H_{56}N_2O_5$<br>Mol. Wt.: 596.85 | |
| 24 | RDHI-043<br>18α | $C_{33}H_{53}NO_3$<br>Mol. Wt.: 511.79 | |
| 25 | RDHI-044<br>18β | $C_{33}H_{53}NO_3$<br>Mol. Wt.: 511.79 | |
| 26 | RDHI-045<br>18α | $C_{38}H_{51}NO_6$<br>Mol. Wt.: 617.83 | |

TABLE 1-1-continued

| Compound No. | Applicant's reference number (RDHI-No.) and denotation of α and β at 18th position | Molecular formula and molecular weight | Structural formula |
|---|---|---|---|
| 27 | RDHI-046 18β | $C_{38}H_{51}NO_6$ Mol. Wt.: 617.83 | |

TABLE 2

| Compound No. | Applicant's reference number (RDHI-No.) | Compound name |
|---|---|---|
| 1 | RDHI-012 | (2S,4aS,6aS,6bR,8aR,12aS,12bR,14bS)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate |
| 2 | RDHI-013 | (2S,4aS,6aS,6bR,8aR,12aS,12bR,14bR)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate |
| 3 | RDHI-014 | 2-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylcarbamoyl)benzoic acid |
| 4 | RDHI-015 | 2-((4aR,6aR,6bS,8aS,11S,12aR,14aR,14bS)-11-(methoxycarbonyl)-4,4,6a,6b,8a,11,12a,14b-octamethyl-14-oxo-1,2,3,4,4a,5,6,6a,6b,7,8,8a,9,10,11,12,12a,14,14a,14b-icosahydropicen-3-ylcarbamoyl)benzoic acid |
| 5 | RDHI-016 | (Z)-4-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylamino)-4-oxobut-2-enoic acid |
| 6 | RDHI-017 | (Z)-4-((4aR,6aR,6bS,8aS,11S,12aR,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylamino)-4-oxobut-2-enoic acid |
| 7 | RDHI-021 | 1-(3S,4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl 2-methyl pyrrolidine-1,2-dicarboxylate |
| 8 | RDHI-022 | 1-(3S,4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl 2-methyl piperidine-1,2-dicarboxylate |
| 9 | RDHI-023 | (2S,4aS,6aS,6bR,8aR,12aS,12bR,14bS)-methyl 10-(3-(2-(methoxycarbonyl)phenyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate |
| 10 | RDHI-024 | (2S,4aS,6aS,6bR,8aR,12aS,12bR,14bS)-methyl 10-(3-(2-ethoxy-2-oxoethyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate |

TABLE 2-continued

| Compound No. | Applicant's reference number (RDHI-No.) | Compound name |
|---|---|---|
| 11 | RDHI-025 | (2S,4aS,6aS,6bR,8aR,12aS,12bR,14bS)-methyl 10-(3-((S)-1-methoxy-1-oxo-3-phenylpropan-2-yl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate |
| 12 | RDHI-026 | 2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)benzoic acid |
| 13 | RDHI-027 | 2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)acetic acid |
| 14 | RDHI-028 | (2S)-2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)-3-phenyl propanoic acid |
| 15 | RDHI-031 | 2-(((3S,4aR,6aR,6bS,8aS,11S,12aS,14aR,14bS)-11-(methoxycarbonylamino)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yloxy)carbonyl)benzoic acid |
| 16 | RDHI-032 | (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide |
| 17 | RDHI-033 | (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide |
| 18 | RDHI-034 | (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide |
| 19 | RDHI-035 | (2S,4aS,6aS,6bR,8aR,12aS,12bR,14bS)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide |
| Intermediate of 19 | RDHI-036 | (2S,4aS,6aS,6bR,8aR,10S,12aS,12bR,14bS)-10-hydroxy-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide |
| Intermediate of 19 | RDHI-037 | (2S,4aS,6aS,6bR,8aR,12aS,12bR,14bS)-2,4a,6a,6b,9,9,12a-heptamethyl-10,13-dioxo-1,2,3,4,4a,5,6,6a,6b,7,8,8a,9,10,11,12,12a,12b,13,14b-icosahydropicene-2-carboxamide |
| Intermediate of 19 | RDHI-038 | (2S,4aS,6aS,6bR,8aR,12aS,12bR,14bS)-10-(hydroxyimino)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide |
| 20 | RDHI-039 | (2S,4aS,6aS,6bR,8aR,12aS,12bR,14bS)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid hydrochloride |
| 21 | RDHI-040 | (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid hydrochloride |
| 22 | RDHI-041 | (2S,4aS,6aS,6bR,8aR,12aS,12bR,14bS)-methyl 2,4a,6a,6b,9,9,12a-heptamethyl-10-(morpholine-4-carboxamido)-13-oxo-1,2,3,4,4a,5,6,6a,6b,7,8,8a,9,10,11,12,12a,12b,13,14b-icosahydropicene-2-carboxylate |
| 23 | RDHI-042 | (2S,4aS,6aS,6bR,8aR,12aS,12bR,14bR)-methyl 2,4a,6a,6b,9,9,12a-heptamethyl-10-(morpholine-4-carboxamido)-13-oxo-1,2,3,4,4a,5,6,6a,6b,7,8,8a,9,10,11,12,12a,12b,13,14b-icosahydropicene-2-carboxylate |
| 24 | RDHI-043 | (2S,4aS,6aS,6bR,8aR,12aS,12bR,14bS)-methyl 10-(dimethylamino)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate |
| 25 | RDHI-044 | (2S,4aS,6aS,6bR,8aR,12aS,12bR,14bR)-methyl 10-(dimethylamino)-2,4a,6a,6b,9,9,12a-heptamethyl-13-oxo- |

TABLE 2-continued

| Compound No. | Applicant's reference number (RDHI-No.) | Compound name |
|---|---|---|
| 26 | RDHI-045 | (2S,4aS,6aS,6bR,8aR,12aS,12bR,14bS)-10-(2-carboxybenzamide)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid |
| 27 | RDHI-046 | (2S,4aS,6aS,6bR,8aR,12aS,12bR,14bR)-10-(2-carboxybenzamide)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid |

Among the compounds presented in Table 1, examples of a more preferred RDH10 enzyme activity inhibitor may include a compound selected from the group consisting of Compound No. 1 (RDHI012): (2S,4aS,6aS,6bR,8aR,12aS,12bR,14bS)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 2 (RDHI013): (2S,4aS,6aS,6bR,8aR,12aS,12bR,14bR)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 3 (RDHI014): 2-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylcarbamoyl)benzoic acid, Compound No. 4 (RDHI015): 2-((4aR,6aR,6bS,8aS,11S,12aR,14aR,14bS)-11-(methoxycarbonyl)-4,4,6a,6b,8a,11,12a,14b-octamethyl-14-oxo-1,2,3,4,4a,5,6,6a,6b,7,8,8a,9,10,11,12,12a,14,14a,14b-icosahydropicen-3-ylcarbamoyl)benzoic acid, Compound No. 5 (RDHI016): (Z)-4-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylamino)-4-oxobut-2-enoic acid, Compound No. 6 (RDHI017): (Z)-4-((4aR,6aR,6bS,8aS,11S,12aR,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylamino)-4-oxobut-2-enoic acid, Compound No. 7 (RDHI021): 1-(3S,4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl 2-methyl pyrrolidine-1,2-dicarboxylate, Compound No. 8 (RDHI022): 1-(3S,4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl 2-methyl piperidine-1,2-dicarboxylate, Compound No. 9 (RDHI023): (2S,4aS,6aS,6bR,8aR,12aS,12bR,14bS)-methyl 10-(3-(2-(methoxycarbonyl)phenyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 10 (RDHI024): (2S,4aS,6aS,6bR,8aR,12aS,12bR,14bS)-methyl 10-(3-(2-ethoxy-2-oxoethyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 11 (RDHI025): (2S,4aS,6aS,6bR,8aR,12aS,12bR,14bS)-methyl 10-(3-((S)-1-methoxy-1-oxo-3-phenylpropan-2-yl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 12 (RDHI026): 2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)benzoic acid, Compound No. 13 (RDHI027): 2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)acetic acid, Compound No. 14 (RDHI028): (2S)-2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)-3-phenyl propanoic acid, Compound No. 15 (RDHI031): 2-(((3S,4aR,6aR,6bS,8aS,11S,12aS,14aR,14bS)-11-(methoxycarbonylamino)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yloxy)carbonyl)benzoic acid, Compound No. 16 (RDHI032): (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, Compound No. 17 (RDHI-033): (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, and Compound No. 18 (RDHI034): (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, or a pharmaceutically acceptable salt or hydrate thereof.

Among the compounds presented in Table 1, examples of a still more preferred RDH10 enzyme activity inhibitor may include Compound No. 1 (RDHI-012): (2S,4aS,6aS,6bR,8aR,12aS,12bR,14bS)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 2 (RDHI-013): (2S,4aS,6aS,6bR,8aR,12aS,12bR,14bR)-methyl 10-amino-2,4a,6a,6b,9,9,12a- heptamethyl-13-oxo-1,2,3,4,4a,5,6,6a,6b,7,8,8a,9,10,11,12,12a,12b,13,14b-icosahydropicene-2-carboxylate, Compound No. 5 (RDHI-016): (Z)-4-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-ylamino)-4-oxobut-2-enoic acid, Compound No. 9 (RDHI-023): (2S,4aS,6aS,6bR,8aR,12aS,12bR,14bS)-methyl 10-(3-(2-(methoxycarbonyl)phenyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 10 (RDHI-024): (2S,4aS,6aS,6bR,8aR,12aS,12bR,14bS)-methyl 10-(3-(2-ethoxy-2-oxoethyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 14 (RDHI-028): (2S)-2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)-3-phenyl propanoic acid, Compound No. 16 (RDHI-032): (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, Compound No. 17 (RDHI-033): (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, Compound No. 18 (RDHI-034): (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, and pharmaceutically acceptable salts and solvates thereof.

Among the compounds presented in Table 1, examples of a yet more preferred RDH10 enzyme activity inhibitor may include Compound No. 1 (RDHI-012): (2S,4aS,6aS,6bR,8aR,12aS,12bR,14bS)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 2 (RDHI-013): (2S,4aS,6aS,6bR,8aR,12aS,12bR,14bR)-methyl 10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate, Compound No. 16 (RDHI-032): (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, Compound No. 17 (RDHI-033): (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, Compound No. 18 (RDHI-034): (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide, and pharmaceutically acceptable salts and solvates thereof.

Preventive and/or Therapeutic Agent for Cancer and/or Infectious Disease

The preventive and/or therapeutic agent for cancer and/or infectious diseases of the present invention contains an inhibitory substance of retinoid metabolic pathway as an active ingredient. The proportion of memory T cells in the T cell population is increased by the inhibition of retinoid metabolic pathway. In a preferred aspect, the preventive and/or therapeutic agent for cancer and/or infectious diseases of the present invention is to enhance the therapeutic effect of cancer by immunotherapy, particularly immunotherapy using a cancer antigen peptide. Examples of the cancer antigen peptide used in cancer immunotherapy may include, various kinds of WT1 peptides, for example, human $WT1_{332}$ (SEQ ID NO: 3, as described in WO 2012/046730 A and the like), $MAGE-A4_{278-299}$ (SEQ ID NO: 4), $survivin_{97-111}$ (SEQ ID NO: 5), and mutant peptides exhibiting activities equivalent to those of these, but are not limited thereto.

In addition, the inhibition of retinoid metabolic pathway brings about not only an increase in the proportion of memory T cells but also an increase in the number of T cells itself. Hence, modulators of retinoid metabolic pathway or retinoic acid signaling system are also effective as adjuvants in the prevention (for example, vaccine) and treatment (for example, immunotherapy) of infectious diseases.

The cancer to be the target of application of the preventive and/or therapeutic agent for cancer and/or infectious diseases of the present invention is not particularly limited and includes carcinoma, sarcoma, hematologic malignancy and the like. In a preferred aspect, the target of application of the agent is various kinds of cancers or tumors which express the WT1 gene, for example, hematopoietic tumors such as leukemia, myelodysplastic syndrome, multiple myeloma, and malignant lymphoma and solid cancers or solid tumors such as gastric cancer, colon cancer, lung cancer, breast cancer, germ cell cancer, liver cancer, skin cancer, bladder cancer, prostate cancer, uterine cancer, cervical cancer, ovarian cancer, and brain tumor.

The infectious diseases to be the target of application of the preventive and/or therapeutic agent for cancer and/or infectious diseases of the present invention are not particularly limited. This is because inhibitory substances of retinoid metabolic pathway bring about strong immunity regardless of the kind of infectious diseases through an increase in the number of T cells and an increase in the proportion of memory T cells. In an aspect, the target of application of the agent can be infectious diseases caused by bacteria, viruses, protozoa and the like.

Immunity Enhancer

As described above, the inhibitory substances of retinoid metabolic pathway bring about not only an increase in the proportion of memory T cells but also an increase in the number of T cells itself. Hence, inhibitory substances of retinoid metabolic pathway can be used as an active ingredient of an immunity enhancer which nonspecifically improves the immunity of a subject.

The agents such as the preventive and/or therapeutic agent for cancer and/or infectious diseases, cancer immunotherapy adjuvant, and immunity enhancer of the present invention described above may contain, for example, a carrier and an excipient in addition to the inhibitory substance of retinoid metabolic pathway which is an active ingredient. The method for administering the preventive and/or therapeutic agent for cancer and/or infectious diseases, cancer immunotherapy adjuvant, and immunity enhancer of the present invention can be appropriately selected depending on the conditions such as the kind of disease, the state of subject, and the target site. Examples of the method may include intradermal administration, subcutaneous administration, intramuscular administration, intravenous administration, nasal administration, and oral administration, but are not limited thereto. The amount of the active ingredient contained in the preventive and/or therapeutic agent for cancer and/or infectious diseases, cancer immunotherapy adjuvant, and immunity enhancer of the present invention, the formulation of these agents, the number of administrations and the like can be appropriately selected depending on the conditions such as the kind of disease, the state of the subject, and the target site.

Method of Producing T Cell Population

The T cell population producing method of the present invention is a method for obtaining a T cell population in which the proportion of memory T cells is increased as compared to a commonly used T cell culturing method by adding an inhibitory substance of retinoid metabolic pathway to a T cell population. In this method, the addition of an inhibitory substance of retinoid metabolic pathway to a T cell population can be performed in vitro or in vivo but is preferably performed in vitro. Examples of in vitro addition may include addition of an inhibitory substance of retinoid metabolic pathway to the medium in which a T cell population is cultured. Examples of in vivo addition may include administration of an inhibitory substance of retinoid metabolic pathway into the body of a subject.

The T cell population created by the T cell population producing method of the present invention can be used to increase the effect of the prevention and/or treatment in the prevention and/or treatment of various diseases, preferably cancer or infectious diseases, particularly the immunotherapy for cancer or infectious diseases.

Method of Treatment and Kit

In the method for preventing and/or treating cancer and/or infectious diseases and the kit for preventing and/or treating cancer and/or infectious diseases of the present invention, an inhibitory substance of retinoid metabolic pathway is concurrently used with other active ingredients in the prevention and/or treatment of cancer or infectious diseases, particularly the immunotherapy for cancer or infectious diseases. Examples of such active ingredients may include, cancer antigens, pathogens of infectious diseases or antigens of the pathogens, and immune cells stimulated or activated by these antigens or pathogens.

The cancer antigen means a surface antigen (so-called tumor specific antigen) which is specifically expressed in cancer cells or tumor cells and a partial peptide of the antigen, and examples thereof may include WT1 protein which is a product of oncogene WT1 and WT1 peptide such as $WT1_{332}$ which is a partial peptide of the protein. Examples of pathogens of infectious diseases may include bacteria, fungi, viruses, and protozoa. Examples of antigens of the pathogens may include proteins expressed on the surface of bacteria, fungi, viruses, and the like, glycoproteins and sugar chains, and cell walls of bacteria and fungi and the constituents thereof (such as lipopolysaccharides). Examples of immune cells stimulated or activated by antigens or pathogens may include antigen-presenting cells (for example, dendritic cells, macrophages, and B cells), and T cells activated by the antigen-presenting cells.

The preventive and/or therapeutic agent for cancer and/or infectious diseases, the cancer immunotherapy adjuvant, and the immunity enhancer of the present invention can be concurrently used with an active ingredient in the prevention and/or treatment of various diseases, preferably cancer or infectious diseases, particularly the immunotherapy for cancer or infectious diseases. Examples of the active ingredient may include, the cancer antigens, pathogens of infectious diseases or antigens of the pathogens, and immune cells stimulated or activated by these antigens or pathogens.

The subject to which the method for increasing the memory T cell proportion, the preventive and/or therapeutic agent for cancer and/or infectious diseases, the cancer immunotherapy adjuvant, the immunity enhancer, the kit for preventing and/or treating cancer and/or infectious diseases, the method for preventing and/or treating cancer and/or infectious diseases, the method for preventing and/or treating infectious diseases, and the method for enhancing immunity of the present invention can be applied is not particularly limited as long as it is an animal having an immune system, particularly an acquired immune system, namely, a vertebrate. Examples of the subject may include humans, mice, rats, dogs, cats, rabbits, horses, cattle, sheep, pigs, goats, and monkeys. In a preferred aspect, the subject is a human.

In the method for preventing and/or treating cancer and/or infectious diseases, the method for preventing and/or treating infectious diseases, and the method for enhancing immunity of the present invention, the effective amount of an inhibitory substance of retinoid metabolic pathway to be administered to a subject and the effective amount of cancer antigens, pathogens of infectious diseases or antigens of the pathogens, or immune cells stimulated or activated by these antigens or pathogens can be appropriately determined depending on the conditions such as the kind of disease, the state of the subject, and the target site and using methods well known to those skilled in the art (including various kinds of non-clinical and/or clinical trials). Examples of the cancer antigens, pathogens of infectious diseases or antigens of the pathogens, or immune cells stimulated or activated by these antigens or pathogens which can be used in the method for preventing and/or treating cancer and/or infectious diseases, the method for preventing and/or treating infectious diseases, and the method for enhancing immunity of the present invention are as described above.

The inhibitory substances of retinoid metabolic pathway of the present invention may be concurrently used with inhibitory substances of retinoic acid signaling system (for example, retinoic acid receptor antagonist, dominant negative mutant protein of retinoic acid receptor, RNA molecule which suppresses the expression of a gene encoding retinoic acid receptor, nucleic acid molecule which produces the RNA molecule, and vectors containing the nucleic acid molecule) and the like.

The present invention will be described specifically and in detail with reference to the following Examples, but Examples should not be construed as limiting the present invention.

Example 1: Example 1: Synthesis of Compound No. 1 RDHI-012(α)

Synthesis of 18α-glycyrrhetinic acid methyl ester 2

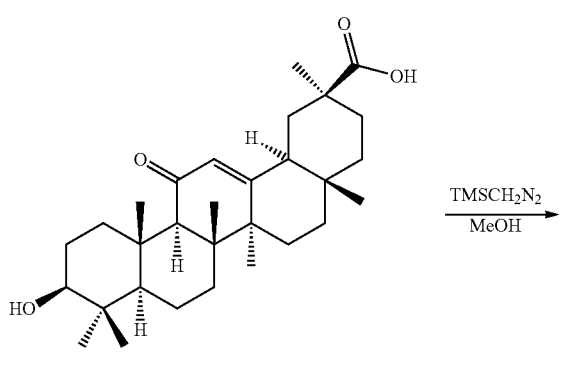

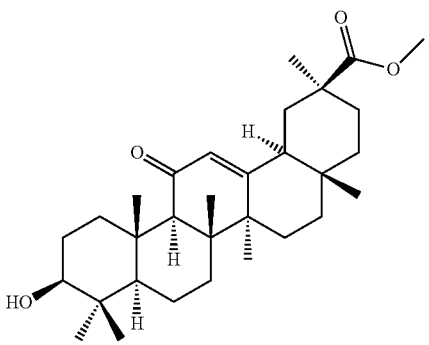

Compound 2 (1.78 g) was dissolved in dimethyl sulfoxide (27 mL) and methylene chloride (27 mL), triethylamine (2.56 mL) and pyridine-sulfur trioxide complex (1.75 g) were added to the solution, and the mixture was stirred at room temperature for 2 hours. The reaction solution was ice-cooled, water was added thereto, the mixture was subjected to extraction using ethyl acetate, and then the organic layer was washed with water and saturated saline solution. The organic layer was dried over sodium sulfate and then concentrated under reduced pressure, the solid thus obtained was slurry-washed with diisopropyl ether and dried under reduced pressure to obtain Compound 3 (1.56 g).

Synthesis of Compound 4

18α-Glycyrrhetinic acid 1 (2 g) was dissolved in methanol (20 mL), TMS diazomethane (9.56 mL) was added to the solution dropwise under ice cooling, and the mixture was stirred at room temperature for 20 minutes.

Furthermore, TMS diazomethane (14.56 mL) was added to the mixture dropwise at room temperature, the mixture was stirred at room temperature for 3 hours, then acetic acid was added thereto, and the mixture was concentrated under reduced pressure. The concentrated solid was slurry-washed with n-hexane/ethyl acetate=1/1, then collected by filtration, and dried under reduced pressure to obtain Compound 2 (1.78 g).

Synthesis of Compound 3

Pyridine (18 mL) and hydroxylamine hydrochloride (1.01 g) were added to Compound 3 (1.56 g) and the mixture was heated at 50° C. for 45 minutes. After the mixture was left to cool, 1 M hydrochloric acid was added thereto, the mixture was subjected to extraction using chloroform, and the organic layer was washed with 2 M hydrochloric acid and saturated saline solution. The organic layer was dried over sodium sulfate and then concentrated under reduced pressure, the solid thus obtained was slurry-washed with diisopropyl ether and dried under reduced pressure to obtain Compound 4 (1.42 g).

Synthesis of Compound No. 1 (RDHI-012) (α)

Example 2: Example 2: Synthesis of Compound No. 2 RDHI-013(β)

Synthesis of 18β-glycyrrhetinic acid methyl ester 6

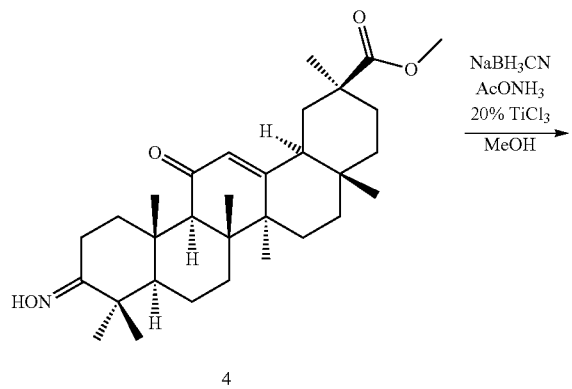

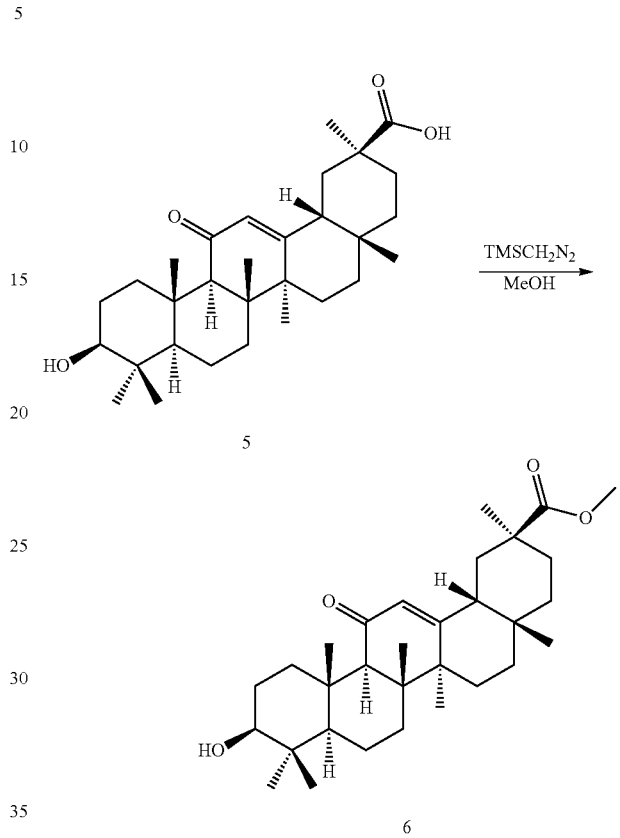

Compound No. 1(RDHI-012)(α)

Methanol (70 mL), ammonium acetate (3.6 g), and sodium cyanoborohydride (0.71 g) were added to Compound 4 (1.42 g), 20% titanium trichloride solution (7.76 mL) was added to the mixture under ice cooling, and the mixture was stirred at room temperature through the night. Furthermore, 20% titanium trichloride solution (7.76 mL) was added thereto, and the mixture was stirred at room temperature through the night. To the reaction mixture, 2 M aqueous sodium hydroxide solution was added until the pH reached about 10, chloroform was added thereto, and the mixture was filtered through Celite. The organic layer of the filtrate was washed with water and saturated saline solution, dried over sodium sulfate, and then concentrated under reduced pressure. The solid obtained was purified by silica gel column chromatography (chloroform/methanol=6/1) to obtain Compound No. 1 (RDHI-012) (α) (1.01 g).

$^1$H-NMR (CDCl$_3$) δ 0.76 (3H, s), 0.81 (3H, s), 0.90 (1H, d, J=3.6 Hz), 0.96 (3H, s), 1.00 (1H, tt, J=2.4 Hz, 13.6 Hz), 1.13-1.21 (11H, m), 1.30-1.56 (9H, m), 1.56-1.72 (2H, m), 1.83 (2H, dt, J=4.4 Hz, 14.0 Hz), 1.90 (1H, dd, J=2.8 Hz, 4.4 Hz), 1.93 (1H, dd, J=2.8 Hz, 4.8 Hz), 1.98-2.10 (3H, m), 2.33 (1H, d, J=8.4 Hz), 2.36 (1H, s), 2.76 (1H, dt, J=4.0 Hz, 13.6 Hz), 3.69 (3H, s), 5.66 (1H, s)

Calcd for C$_{31}$H$_{49}$NO$_3$: 483.37, Found: 484.43, [M+H], (positive-ESI).

18β-Glycyrrhetinic acid 5 (5 g) was dissolved in methanol (40 mL), TMS diazomethane (10.6 mL) was added to the solution dropwise under ice cooling, and the mixture was stirred at room temperature for 2 hours. Furthermore, TMS diazomethane (10.6 mL) was added to the mixture dropwise at room temperature, the mixture was stirred at room temperature for 1 hour, then acetic acid was added thereto, and the mixture was concentrated under reduced pressure. The concentrated solid was slurry-washed with n-hexane/ethyl acetate=1/1, then collected by filtration, and dried under reduced pressure to obtain Compound 6 (2.3 g).

Synthesis of Compound 7

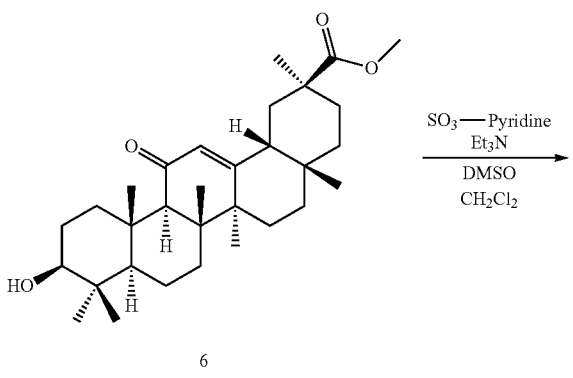

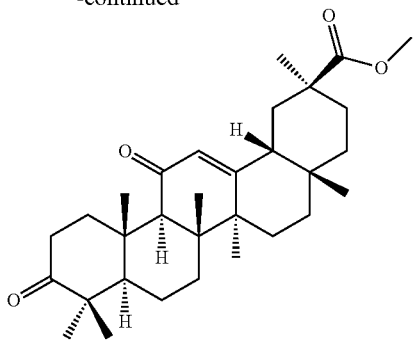

7

Compound 6 (0.50 g) was dissolved in dimethyl sulfoxide (7.6 mL) and methylene chloride (7.6 mL), triethylamine (0.72 mL) and pyridine-sulfur trioxide complex (0.49 g) were added to the solution, and the mixture was stirred at room temperature for 4 hours. The reaction solution was ice-cooled, water was added thereto, the mixture was subjected to extraction using ethyl acetate, and then the organic layer was washed with water and saturated saline solution. The organic layer was dried over sodium sulfate and then concentrated under reduced pressure, the solid thus obtained was slurry-washed with diisopropyl ether and dried under reduced pressure to obtain Compound 7 (0.40 g).

Synthesis of Compound 8

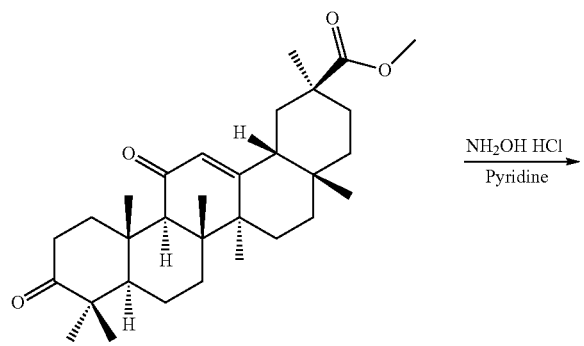

Pyridine (4.5 mL) and hydroxylamine hydrochloride (0.26 g) were added to Compound 7 (0.40 g) and the mixture was heated at 50° C. for 1 hour. After the mixture was left to cool, 2 M hydrochloric acid was added thereto, the mixture was subjected to extraction using chloroform, and the organic layer was washed with 2 M hydrochloric acid and saturated saline solution. The organic layer was dried over sodium sulfate and then concentrated under reduced pressure, the solid thus obtained was slurry-washed with diisopropyl ether and dried under reduced pressure to obtain Compound 8 (0.35 g).

Synthesis of Compound No. 2 RDHI-013(β)

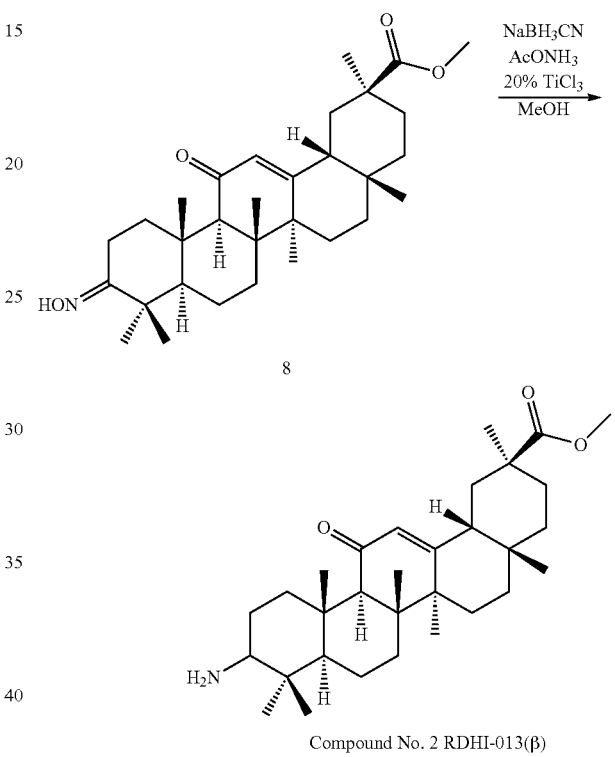

Compound No. 2 RDHI-013(β)

Methanol (15 mL), ammonium acetate (0.75 g), and sodium cyanoborohydride (0.81 g) were added to Compound 8 (0.30 g), 20% titanium trichloride solution (1.62 mL) was added to the mixture under ice cooling, and the mixture was stirred at room temperature for 1 hour. Furthermore, 20% titanium trichloride solution (1.62 mL) was added thereto, and the mixture was stirred at room temperature through the night. To the reaction mixture, 2 M aqueous sodium hydroxide solution was added until the pH reached about 10, chloroform was added thereto, and the mixture was filtered through Celite. The organic layer of the filtrate was washed with water and saturated saline solution, dried over sodium sulfate, and then concentrated under reduced pressure. The solid obtained was purified by silica gel column chromatography (chloroform/methanol=6/1) to obtain Compound No. 2 RDHI-013(β) (0.17 g).

$^1$H-NMR (CDCl$_3$) δ 0.76 (3H, s), 0.81 (3H, s), 0.91 (1H, d, J=6.4 Hz), 0.97 (3H, s), 1.00 (1H, tt, J=2.4 Hz, 13.6 Hz), 1.13-1.24 (11H, m), 1.30-1.54 (9H, m), 1.58-1.72 (2H, m), 1.83 (2H, dt, J=4.4 Hz, 14.0 Hz), 1.90 (1H, dd, J=2.8 Hz, 4.4 Hz), 1.94 (1H, dd, J=2.8 Hz, 4.4 Hz), 1.98-2.03 (2H, m), 2.07 (1H, dd, J=3.6 Hz, 12.0 Hz), 2.36 (2H, s), 2.76 (1H, dt, J=3.6 Hz, 13.2 Hz), 3.69 (3H, s), 5.66 (1H, s)

Calcd for $C_{31}H_{49}NO_3$: 483.37, Found: 484.43, [M+H], (positive-ESI).

Example 3: Example 3: Synthesis of Compound No. 3 RDHI-014(α)

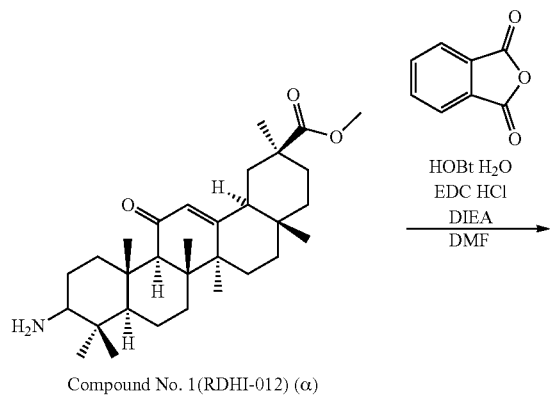

Compound No. 1(RDHI-012) (α)

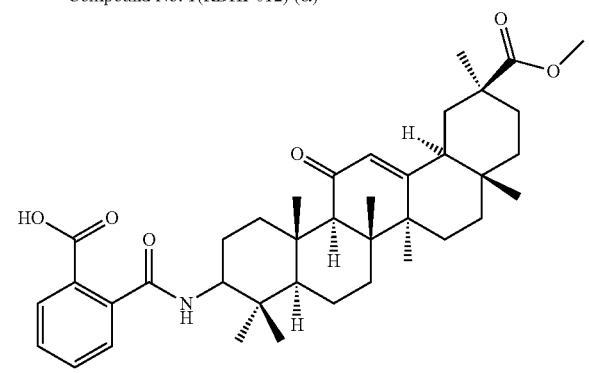

Compound No. 3 RDHI-014(α)

Phthalic anhydride (34 mg), 1-hydroxybenzotriazole monohydrate (38 mg), and N,N-dimethylformamide (10 mL) were added to Compound No. 1 (RDHI-012)(α) (100 mg), and the mixture was ice-cooled. Thereto, 1-ethyl-3-(3-dimethylaminopropyl)carbodiimide hydrochloride (44 mg) and diisopropylethylamine (40 mg) were added, and the mixture was stirred at room temperature for 2 hours. Water was added to the reaction solution, the mixture was subjected to extraction using ethyl acetate, and the organic layer was washed with water and saturated saline solution. The organic layer was dried over sodium sulfate and then concentrated under reduced pressure, and the solid thus obtained was purified by silica gel column chromatography (hexane/ethyl acetate=5/1) to obtain Compound No. 3 RDHI-014(α) (0.90 mg).

$^1$H-NMR (CDCl$_3$) δ 0.82 (3H, s), 0.84 (3H, s), 0.80-0.90 (2H, m), 1.03 (3H, s), 0.99-1.15 (2H, m), 1.16 (3H, s), 1.16 (3H, s), 1.23 (3H, s), 1.40 (3H, s), 1.10-1.50 (8H, m), 1.50-1.75 (2H, m), 1.84 (2H, dt, J=4.4 Hz, 13.6 Hz), 1.91-2.10 (3H, m), 2.43 (1H, s), 2.85 (1H, dt, J=3.6 Hz, 13.6 Hz), 3.69 (3H, s), 3.75 (1H, dd, J=4.4 Hz, 12.0 Hz), 5.68 (1H, s), 7.69 (1H, dt, J=1.2 Hz, 7.6 Hz), 7.77 (1H, dt, J=1.2 Hz, 7.6 Hz), 7.95 (2H, ddt, J=0.8 Hz, 7.6 Hz, 14.8 Hz)

Calcd for $C_{39}H_{53}NO_5$: 631.39, Found: 632.57, [M+H]$_r$ (positive-ESI).

Example 4: Example 4: Synthesis of Compound No. 4 RDHI-015(β)

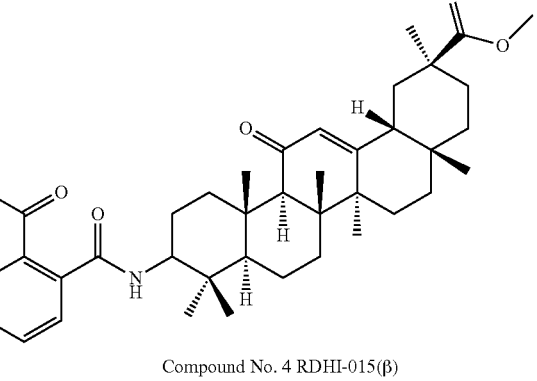

Compound No. 1 RDHI-013(β)

Compound No. 4 RDHI-015(β)

N,N-dimethylformamide (10 mL) was added to Compound No. 2 (RDHI-013)(β) (100 mg), phthalic anhydride (34 mg), O-(7-azabenzotriazol-1-yl)-N,N,N',N'-tetramethyluronium hexafluorophosphate (87 mg), and diisopropylethylamine (53 mg) were added thereto, and the mixture was stirred at room temperature for 2 hours. Saturated sodium bicarbonate water was added to the reaction solution, the mixture was subjected to extraction using ethyl acetate, and then the organic layer was washed with saturated saline solution. The organic layer was dried over sodium sulfate and then concentrated under reduced pressure, and the solid thus obtained was purified by silica gel column chromatography (hexane/ethyl acetate=5/1 to 1/1) to obtain Compound No. 4 RDHI-015(β) (110 mg).

$^1$H-NMR (CDCl$_3$) δ 0.82 (3H, s), 0.84 (3H, s), 0.80-0.90 (2H, m), 1.03 (3H, s), 0.99-1.15 (2H, m), 1.16 (3H, s), 1.16 (3H, s), 1.23 (3H, s), 1.40 (3H, s), 1.10-1.50 (8H, m), 1.50-1.75 (2H, m), 1.84 (2H, dt, J=4.4 Hz, 13.6 Hz), 1.91-2.10 (3H, m), 2.43 (1H, s), 2.85 (1H, dt, J=3.6 Hz, 13.6 Hz), 3.69 (3H, s), 3.75 (1H, dd, J=4.4 Hz, 12.0 Hz), 5.68 (1H, s), 7.69 (1H, dt, J=1.2 Hz, 7.6 Hz), 7.77 (1H, dt, J=1.2 Hz, 7.6 Hz), 7.95 (2H, ddt, J=0.8 Hz, 7.6 Hz, 14.8 Hz)

Calcd for $C_{39}H_{53}NO_6$: 631.39, Found: 632.57, [M+H], (positive-ESI).

Example 5: Example 5: Synthesis of Compound No. 5 RDHI-016(α)

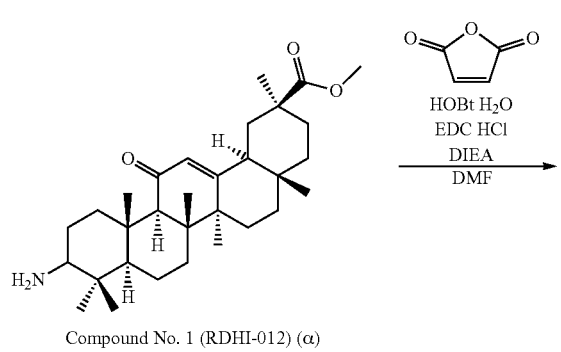

Example 6: Example 6: Synthesis of Compound No. 6 RDHI-017(β)

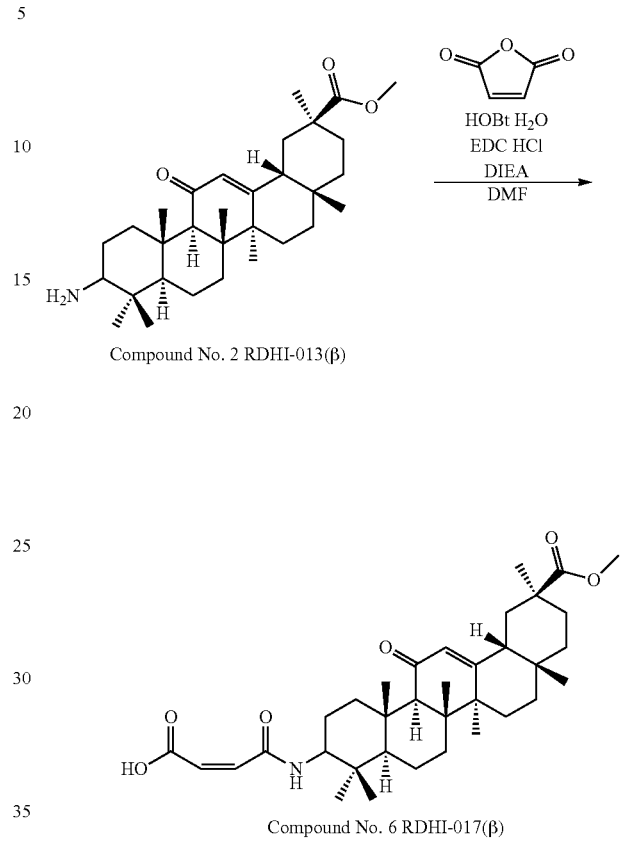

Maleic anhydride (22 mg), 1-hydroxybenzotriazole monohydrate (38 mg), and N,N-dimethylformamide (10 mL) were added to Compound No. 1 (RDHI-012)(α) (100 mg), and the mixture was ice-cooled. Thereto, 1-ethyl-3-(3-dimethylaminopropyl)carbodiimide hydrochloride (44 mg) and diisopropylethylamine (40 mg) were added, and the mixture was stirred at room temperature for 3 hours. Water was added to the reaction solution, the mixture was subjected to extraction using ethyl acetate, and then the organic layer was washed with water and saturated saline solution. The organic layer was dried over sodium sulfate and then concentrated under reduced pressure, and the solid thus obtained was purified by silica gel column chromatography (hexane/ethyl acetate=5/1 to methanol) to obtain Compound No. 5 RDHI-016(α) (60 mg).

$^1$H-NMR (DMSO-$d_6$) δ 0.76 (3H, s), 0.80 (3H, s), 0.81 (3H, s), 0.81-1.02 (2H, m), 1.06 (3H, m), 1.11 (3H, s), 1.02-1.30 (5H, m), 1.38 (3H, s), 1.30-1.50 (6H, m), 1.50-1.60 (2H, m), 1.73 (2H, d, J=9.2 Hz), 1.60-1.90 (3H, m), 2.02 (1H, t, J=13.2 Hz), 2.11 (1H, t, J=9.2 Hz), 2.41 (1H, s), 2.52-2.70 (1H, m), 3.51 (1H, s), 5.44 (2H, d, J=2.8 Hz), 6.03 (1H, d, J=13.2 Hz)

Calcd for $C_{35}H_{51}NO_6$: 581.37, Found: 582.47, [M+H], (positive-ESI).

Maleic anhydride (22 mg), 1-hydroxybenzotriazole monohydrate (38 mg), and N,N-dimethylformamide (10 mL) were added to Compound No. 2 RDHI-013(β) (100 mg), and the mixture was ice-cooled. Thereto, 1-ethyl-3-(3-dimethylaminopropyl)carbodiimide hydrochloride (44 mg) and diisopropylethylamine (40 mg) were added, and the mixture was stirred at room temperature for 4 hours. Water was added to the reaction solution, the mixture was subjected to extraction using ethyl acetate, and then the organic layer was washed with water and saturated saline solution. The organic layer was dried over sodium sulfate and then concentrated under reduced pressure, and the solid thus obtained was slurry-washed with hexane/ethyl acetate=1/1 to obtain Compound No. 6 RDHI-017(β) (67 mg).

$^1$H-NMR (DMSO-$d_6$) δ 0.76 (3H, s), 0.79 (3H, s), 0.82 (3H, s), 0.89-0.98 (2H, m), 1.04 (3H, s), 1.07 (3H, s), 1.11 (3H, s), 1.18 (2H, t, J=6.8 Hz), 1.39 (3H, s), 1.32-1.50 (6H, m), 1.54 (2H, d, J=10.4 Hz), 1.73 (2H, d, J=9.6 Hz), 1.59-1.88 (3H, m), 2.11 (2H, t, J=10.8 Hz), 2.43 (1H, s), 2.65 (1H, m), 3.64 (1H, s), 5.32 (1H, s), 6.23 (1H, d, J=9.2 Hz), 6.47 (1H, d, J=6.0 Hz)

Calcd for $C_{35}H_{51}NO_6$: 581.37, Found: 582.47, [M+Fi], (positive-ESI).

Example 7: Example 7: Synthesis of Compound No. 7 RDHI-021(α)

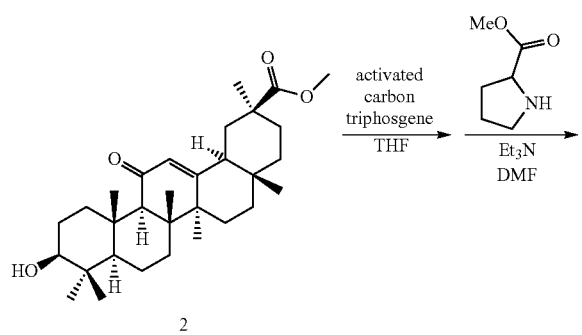

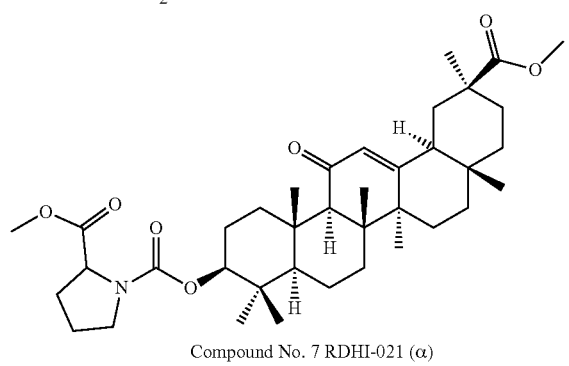

Compound No. 7 RDHI-021 (α)

Tetrahydrofuran (2 mL), triphosgene (98 mg), and activated carbon (3.2 mg) were added to Compound 2 (40 mg), and the mixture was stirred through the night. The reaction solution was filtered to remove the activated carbon, and the filtrate was concentrated under reduced pressure. N,N-dimethylformamide (1.5 mL), L-proline methyl ester hydrochloride (16 mg), and triethylamine (25 mg) were added to the concentrate, and the mixture was stirred at room temperature for 4.5 hours. A 5% aqueous citric acid solution was added to the reaction solution, the mixture was subjected to extraction using ethyl acetate, and then the organic layer was washed with water and saturated saline solution. The organic layer was dried over sodium sulfate and then concentrated under reduced pressure, and the solid thus obtained was purified by silica gel column chromatography (hexane/ethyl acetate=4/1 to 1/1) and HPLC fractionation (water [0.05% TFA]/acetonitrile [0.05% TFA]=90/10 to 1/99) using an ODS column to obtain Compound No. 7 RDHI-021(α) (22 mg).

Calcd for $C_{38}H_{57}NO_7$: 639.41, Found: 640.51, [M+H], (positive-ESI).

Example 8: Example 8: Synthesis of Compound No. 8 RDHI-022(α)

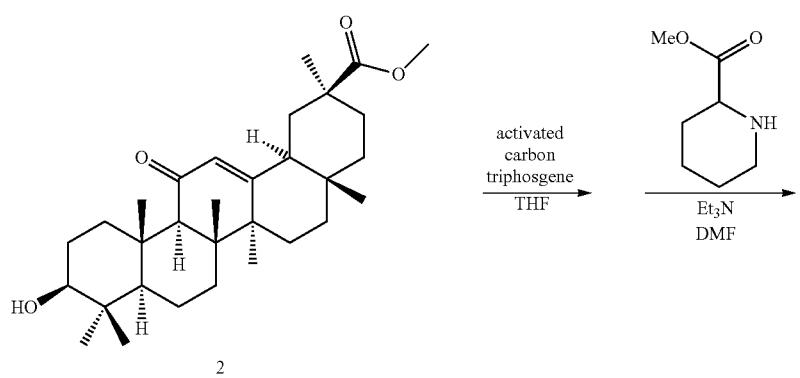

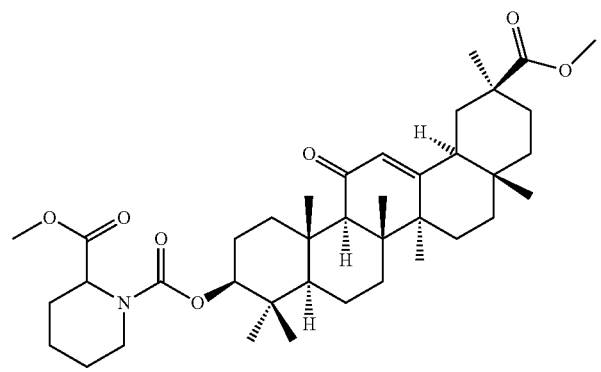

Compound No. 8 RDHI-022(α)

Tetrahydrofuran (2 mL), triphosgene (98 mg), and activated carbon (3.2 mg) were added to Compound 2 (40 mg), and the mixture was stirred through the night. The reaction solution was filtered to remove the activated carbon, and the filtrate was concentrated under reduced pressure. N,N-dimethylformamide (1.5 mL), methyl piperidine-2-carboxylate (14 mg), and triethylamine (17 µL) were added to the concentrate, and the mixture was stirred at room temperature for 3.5 hours. A 5% aqueous citric acid solution was added to the reaction solution, the mixture was subjected to extraction using ethyl acetate, and then the organic layer was washed with water and saturated saline solution. The organic layer was dried over sodium sulfate and then concentrated under reduced pressure, and the solid thus obtained was purified by HPLC fractionation (water/acetonitrile=90/10 to 1/99) using an ODS column to obtain Compound No. 8 RDHI-022(α) (21 mg).

Calcd for $C_{39}H_{59}NO_7$: 653.43, Found: 654.56, [M+H], (positive-ESI).

Example 9: Example 9: Synthesis of Compound No. 9 RDHI-023(α)

Tetrahydrofuran (1 mL) and methyl 2-isocyanatobenzoate (18 mg) were added to Compound No. 1 (RDHI-012)(α) (50 mg), and the mixture was stirred at room temperature through the night. Water (1 mL) was added to the reaction mixture, the mixture was concentrated under reduced pressure, and the solid thus obtained was purified by silica gel column chromatography (hexane/ethyl acetate=5/1) to obtain Compound No. 9 RDHI-023(α) (15 mg).

Calcd for $C_{40}H_{56}N_2O_6$: 660.41, Found: 661.74, [M+H], (positive-ESI).

Example 10: Example 10: Synthesis of Compound No. 10 RDHI-024(α)

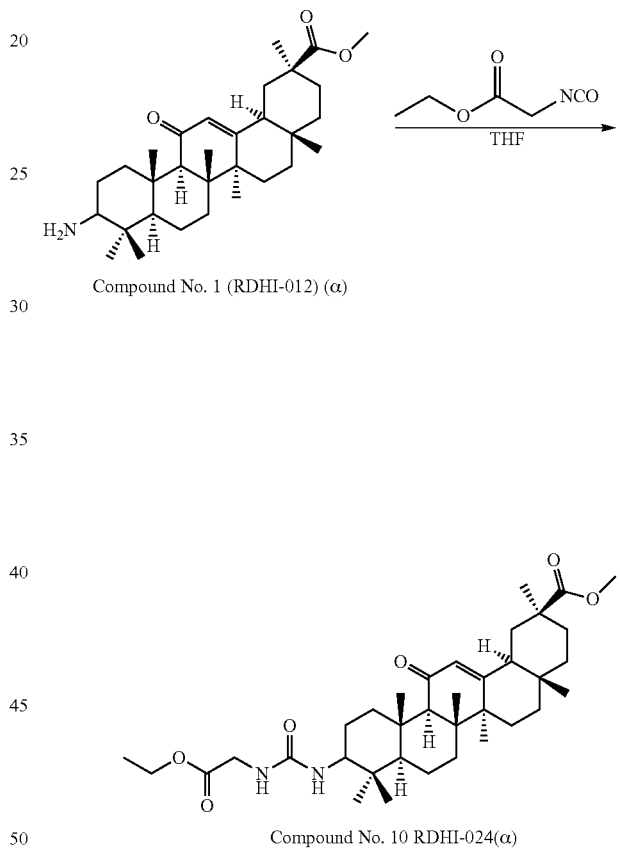

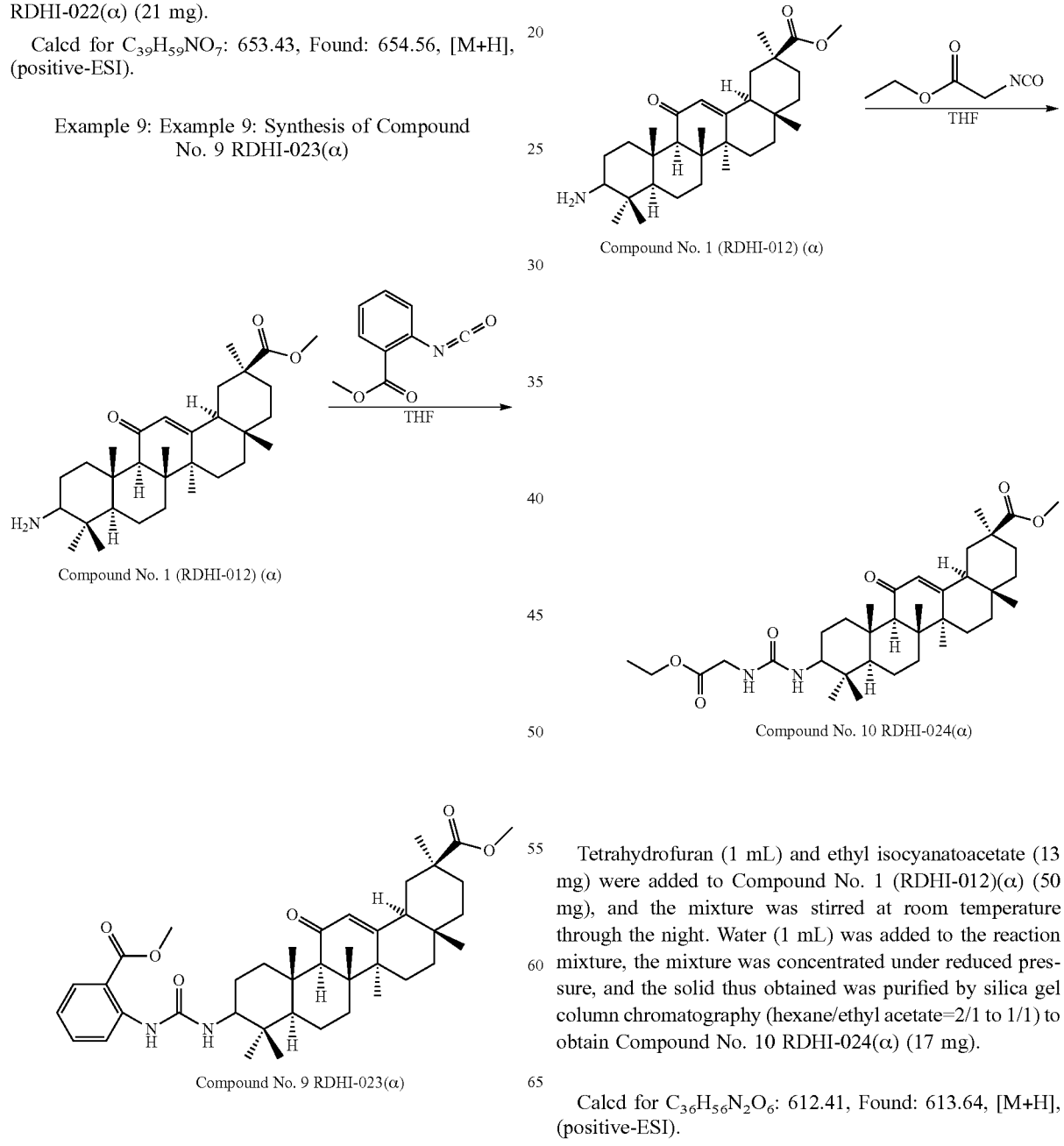

Tetrahydrofuran (1 mL) and ethyl isocyanatoacetate (13 mg) were added to Compound No. 1 (RDHI-012)(α) (50 mg), and the mixture was stirred at room temperature through the night. Water (1 mL) was added to the reaction mixture, the mixture was concentrated under reduced pressure, and the solid thus obtained was purified by silica gel column chromatography (hexane/ethyl acetate=2/1 to 1/1) to obtain Compound No. 10 RDHI-024(α) (17 mg).

Calcd for $C_{36}H_{56}N_2O_6$: 612.41, Found: 613.64, [M+H], (positive-ESI).

Example 11: Example 11: Synthesis of Compound No. 11 RDHI-025(α)

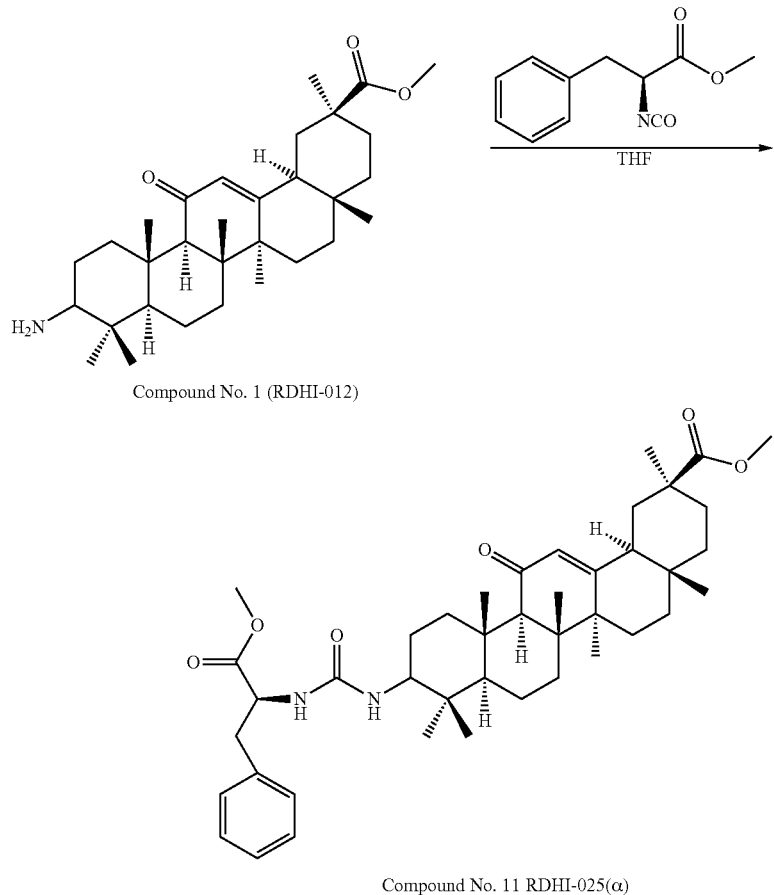

Tetrahydrofuran (1 mL) and methyl (S)-2-isocyanato-3-phenylpropionate (21 mg) were added to Compound No. 1 (RDHI-012)(α) (50 mg), and the mixture was stirred at room temperature through the night. Water (1 mL) was added to the reaction solution, the mixture was concentrated under reduced pressure, and the solid thus obtained was purified by silica gel column chromatography (hexane/ethyl acetate=2/1 to 0/1) to obtain Compound No. 11 RDHI-025(α) (28 mg).

Calcd for $C_{42}H_{60}N_2O_6$: 688.45, Found: 689.82, $[M+H]_f$ (positive-ESI).

Example 12: Example 12: Synthesis of Compound No. 12 RDHI-026(α)

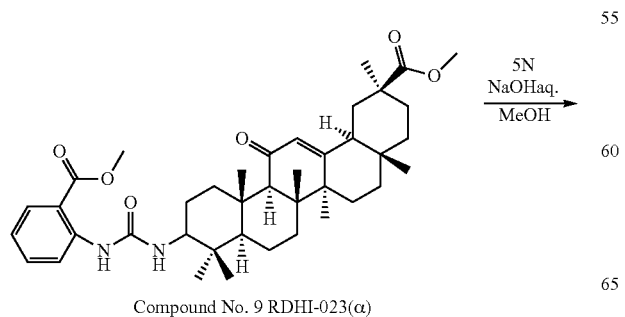

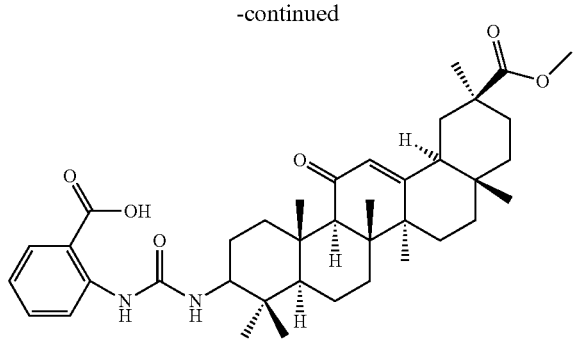

Compound No. 12 RDHI-026(α)

Methanol (1 mL) and 5 M aqueous sodium hydroxide solution (56 μL) were added to Compound No. 9 RDHI-023(α) (46 mg), and the mixture was stirred at 40° C. through the night. Furthermore, 5 M aqueous sodium hydroxide solution (56 μL) was added thereto, and the mixture was stirred at 40° C. through the night. To the reaction solution, 3 M hydrochloric acid was added, the mixture was concentrated under reduced pressure, and the solid thus obtained was purified by silica gel column chromatography (hexane/ethyl acetate=2/1) to obtain Compound No. 12 RDHI-026(α) (43 mg).

Calcd for $C_{39}H_{54}N_2O_6$: 646.40, Found: 647.69, [M+H], (positive-ESI).

Example 13: Example 13: Synthesis of Compound No. 13 RDHI-027(α)

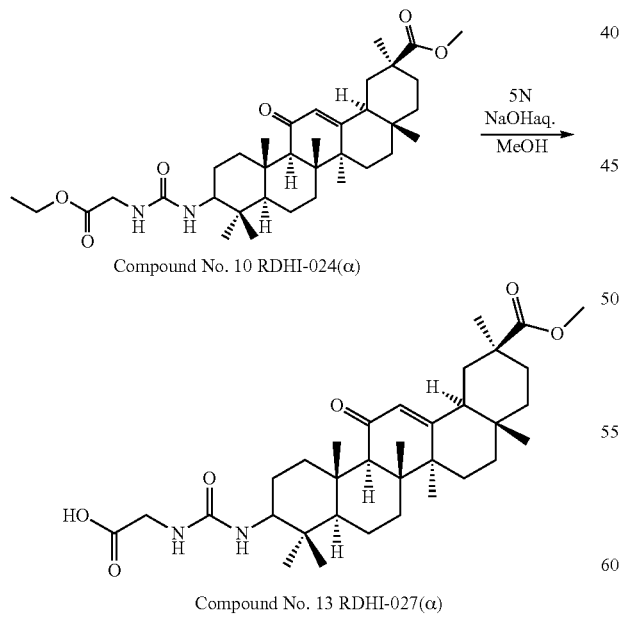

Methanol (3 mL) and 5 M aqueous sodium hydroxide solution (111 μL) were added to Compound No. 10 RDHI-024(α) (42 mg), and the mixture was stirred at 40° C. through the night. To the reaction solution, 3 M hydrochloric acid was added, the mixture was concentrated under reduced pressure, and the solid thus obtained was purified by silica gel column chromatography (hexane/ethyl acetate=1/2 to 0/1) to obtain Compound No. 13 RDHI-027(α) (12 mg).

Calcd for $C_{34}H_{52}N_2O_6$ 584.38, Found: 585.62, [M+H], (positive-ESI).

Example 14

Example 14: Synthesis of Compound No. 14 RDHI-028(α)

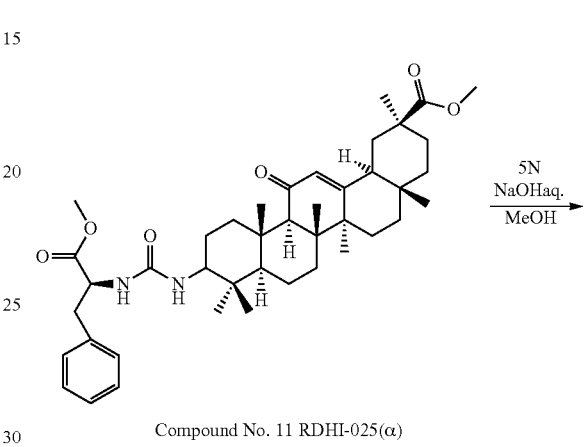

Compound No. 11 RDHI-025(α)

Compound No. 14 RDHI-028(α)

Methanol (3 mL) and 5 M aqueous sodium hydroxide solution (146 μL) were added to Compound No. 11 RDHI-025(α) (62 mg), and the mixture was stirred at 40° C. through the night. To the reaction solution, 3 M hydrochloric acid and water were added, the mixture was subjected to extraction using ethyl acetate, and the organic layer was washed with saturated saline solution. The organic layer was dried over anhydrous sodium sulfate and then concentrated under reduced pressure, and the solid thus obtained was purified by silica gel column chromatography (hexane/ethyl acetate=1/2 to 0/1) to obtain Compound No. 14 RDHI-028 (α) (64 mg).

Calcd for $C_{41}H_{58}N_2O_6$ 674.43, Found: 675.71, [M+H], (positive-ESI).

Example 15: Example 15: Synthesis of Compound No. 15 RDHI-031(α)

Synthesis of Compound 10

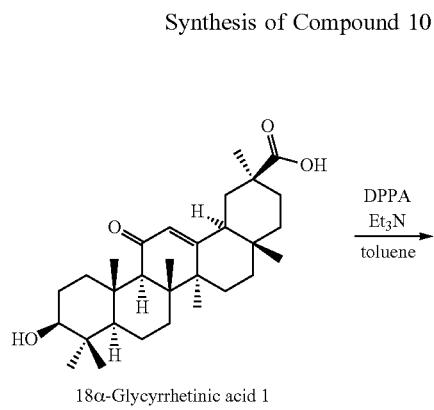

18α-Glycyrrhetinic acid 1

Toluene (2.5 mL), triethylamine (33 mg), and diphenylphosphoryl azide (88 mg) were added to 18α-glycyrrhetinic acid 1 (100 mg), and the mixture was stirred at 105° C. for 20 minutes. Methanol was added to the reaction solution, the mixture was stirred at room temperature through the night, and the reaction solution was concentrated under reduced pressure. Water was added to the concentrate, the mixture was subjected to extraction using ethyl acetate, and the organic layer was washed with saturated saline solution. The organic layer was dried over anhydrous sodium sulfate and then concentrated under reduced pressure, and the solid thus obtained was slurry-washed with hexane to obtain Compound 10 (96 mg).

Synthesis of Compound No. 15 RDHI-031(α)

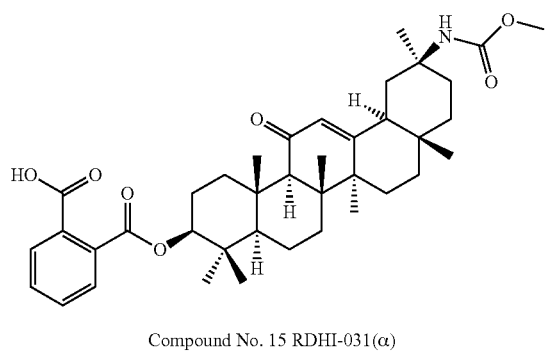

Compound No. 15 RDHI-031(α)

Tetrahydrofuran (7 mL), phthalic anhydride (35 mg), and N,N-dimethyl-4-aminopyridine (3 mg) were added to Compound 10 (90 mg), and the mixture was stirred at room temperature through the night. Water was added to the reaction solution, the mixture was subjected to extraction using ethyl acetate, and the organic layer was washed with saturated saline solution. The organic layer was dried over anhydrous sodium sulfate and then concentrated under reduced pressure, and the solid thus obtained was purified by silica gel column chromatography (ethyl acetate). Furthermore, the solid purified was slurry-washed with water and ethanol to obtain Compound No. 15 RDHI-031(α) (93 mg).

Calcd for $C_{39}H_{53}NO_7$: 647.38, Found: 648.55, [M+H], (positive-ESI).

Example 16

Example 16: Synthesis of Compound No. 16 RDHI-032(β)

Synthesis of Compound 11

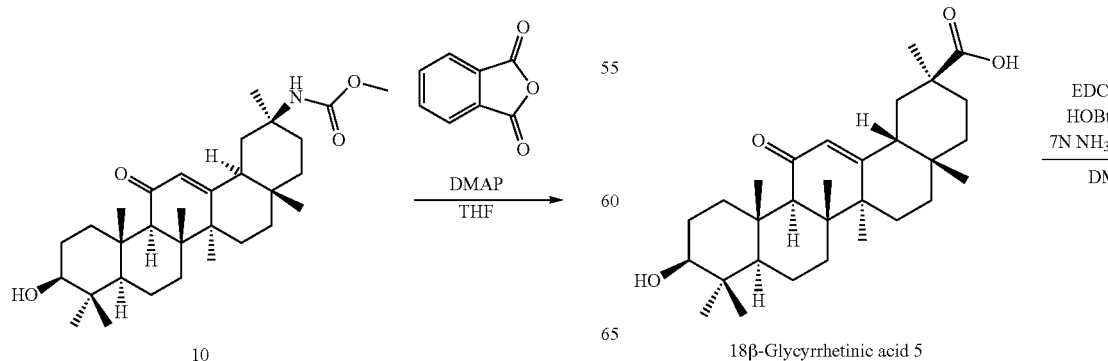

18β-Glycyrrhetinic acid 5

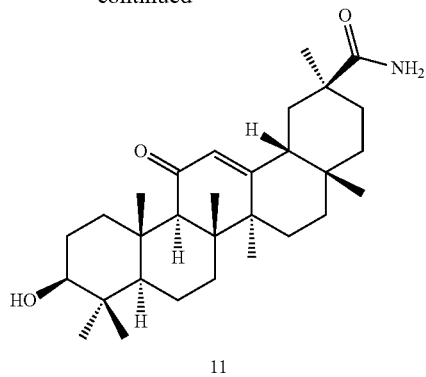

11

18β-Glycyrrhetinic acid 5 (1.50 g) was dissolved in N,N-dimethylformamide (10 mL), HOBt.H₂O (537.4 mg) was added to the solution, EDCHCl (672.9 mg) was added to the mixture under ice cooling, and the mixture was stirred at room temperature for 1 hour. Furthermore, 7 M ammonia/methanol (6.8 mL) was added thereto at room temperature, and the mixture was stirred at room temperature through the night. The mixture was slurry-washed with water and ethyl acetate, then collected by filtration, and dried under reduced pressure to obtain Compound 11 (1.61 g).

Synthesis of Compound 12

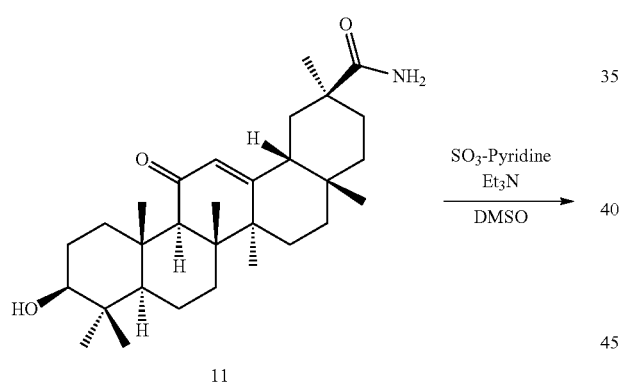

Compound 11 (1.50 g) was dissolved in dimethyl sulfoxide (23 mL), triethylamine (2.2 mL) and pyridine-sulfur trioxide complex (1.52 g) were added to the solution, and the mixture was stirred at room temperature for 3 hours and then stirred at 30° C. for 4 days. The reaction mixture was slurry-washed with water and ethyl acetate, then collected by filtration, and dried under reduced pressure to obtain Compound 12 (1.39 g).

Synthesis of Compound 13

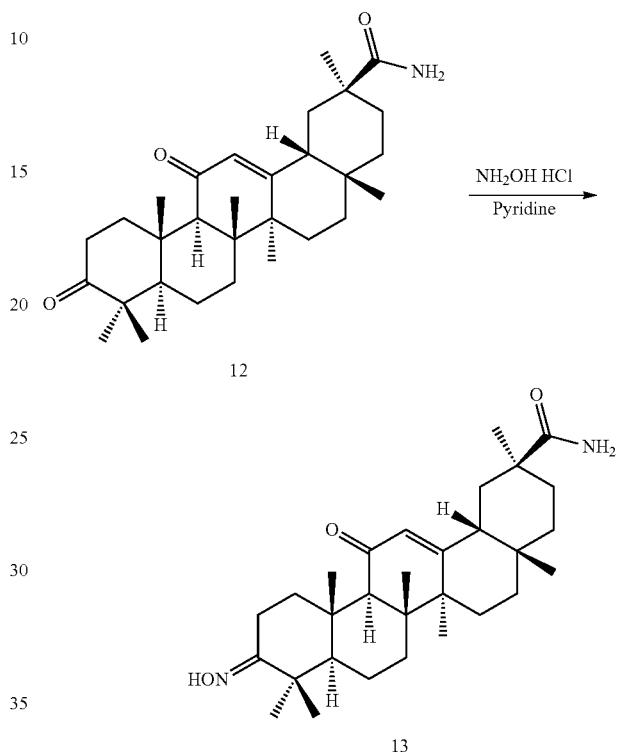

Pyridine (15 mL) and hydroxylamine hydrochloride (0.93 g) were added to Compound 12 (1.39 g), and the mixture was heated at 50° C. for 1 hour. After the mixture was left to cool, 1 M hydrochloric acid was added thereto, the mixture was subjected to extraction using chloroform, and the organic layer was washed with saturated saline solution. The organic layer was dried over sodium sulfate and then under reduced pressure to obtain Compound 13 (0.76 g).

Synthesis of Compound No. 16 RDHI-032(β)

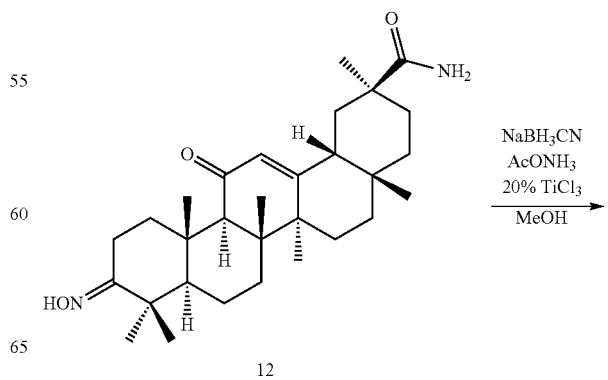

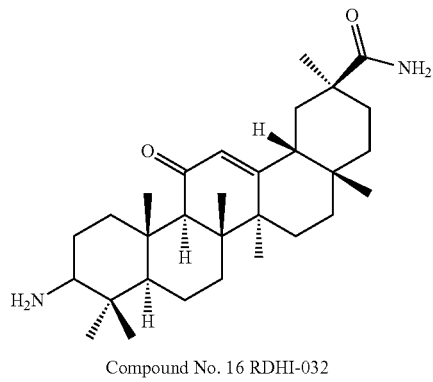

Compound No. 16 RDHI-032

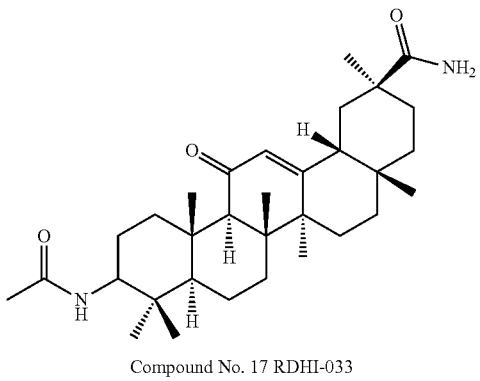

Compound No. 17 RDHI-033

Methanol (40 mL), ammonium acetate (1.98 g), and sodium cyanoborohydride (394.6 mg) were added to Compound 13 (0.76 g) obtained in the step (3), 20% titanium trichloride solution (4.12 g) was added to the mixture under ice cooling, and the mixture was stirred at room temperature for 4 hours. Furthermore, 20% titanium trichloride solution (4.12 g) was added thereto, and the mixture was stirred at room temperature through the night. To the reaction mixture, 2 M aqueous sodium hydroxide solution was added until the pH reached about 10, chloroform was added thereto, and the mixture was filtered through Celite. The organic layer of the filtrate was washed with water and saturated saline solution, dried over sodium sulfate, and then concentrated under reduced pressure to obtain Compound No. 16 RDHI-032(β) (0.42 g).

$^1$H-NMR (DMSO-d$_6$) δ 0.66 (3H, s), 0.70 (2H, d, J=12.4 Hz), 0.74 (3H, s), 0.90 (3H, s), 1.03-1.12 (11H, m), 1.23-1.42 (9H, m), 1.56 (5H, m), 1.75-1.87 (2H, m). 1.98 (2H, m), 2.20 (1H dd, J=4.4 Hz, 10.0 Hz), 2.33 (1H, s), 2.58 (1H, d, J=12.4 Hz), 5.47 (1H, s), 6.77 (1H, s), 7.13 (1H, s), 8.32 (1H, s)

Calcd for $C_{30}H_{48}N_2O_2$: 468.37, Found: 469.24, [M+H], (positive-ESI)

Example 17

Example 17: Example 17: Synthesis of Compound No. 17 RDHI-033(β)

N,N-dimethylformamide (10 mL), acetic acid (13.2 μL), and 1-hydroxybenzotriazole monohydrate (38.3 mg) were added to Compound No. 16 RDHI-032(β) (100 mg), 1-ethyl-3-(3-dimethylaminopropyl)carbodiimide hydrochloride (44.1 mg) and N,N-diisopropylethylamine (55.7 μL) were added thereto under ice cooling, and the mixture was stirred at room temperature through the night. Water was added thereto, the mixture was subjected to extraction using ethyl acetate, and the organic layer was washed with water and saturated saline solution. The organic layer was dried over sodium sulfate and then under reduced pressure, and the solid thus obtained was purified by reversed-phase fractionation to obtain Compound No. 17 RDHI-033(β) (66.2 mg).

$^1$H-NMR (DMSO-d$_6$) δ 0.74 (6H, s), 0.77 (2H, s), 0.87 (3H, s), 0.93-1.15 (11H, m), 1.29-1.43 (9H, m), 1.55 (2H, m), 1.75 (2H, s), 1.82 (3H, s), 1.87 (3H, s), 2.08 (2H, s), 2.41 (1H, s), 2.62 (1H, d, J=13.2 Hz), 3.49 (1H×5/7, d, J=8.0 Hz), 3.63 (1H×2/7, d, J=3.6 Hz), 5.48 (1H, m), 6.77 (1H, s), 7.13 (1H, s), 7.41 (1H×5/7, d, J=8.4 Hz), 7.65 (1H×2/7, d, J=9.6 Hz)

Calcd for $C_{32}H_{50}N_2O_3$: 510.38, Found: 511.65, [M+H], (positive-ESI).

Example 18: Example 18: Synthesis of Compound No. 18 RDHI-034(β)

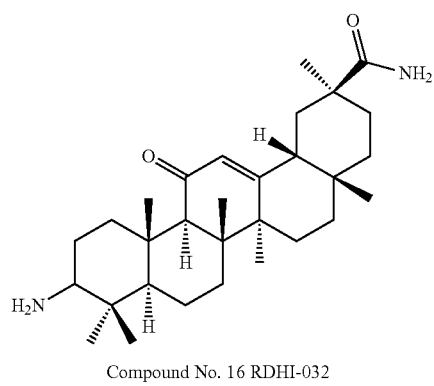

Compound No. 16 RDHI-032

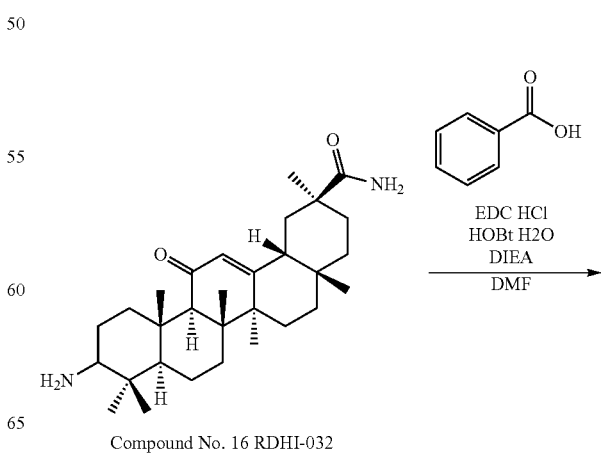

Compound No. 16 RDHI-032

-continued

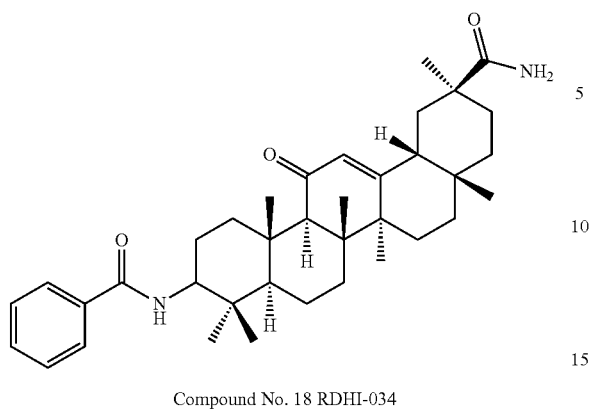

Compound No. 18 RDHI-034

N,N-dimethylformamide (10 mL), benzoic acid (28.1 mg), and 1-hydroxybenzotriazole monohydrate (38.3 mg) were added to Compound No. 16 RDHI-032(β) (100 mg), 1-ethyl-3-(3-dimethylaminopropyl)carbodiimide hydrochloride (44.1 mg) and N,N-diisopropylethylamine (55.7 µL) were added thereto under ice cooling, and the mixture was stirred at room temperature for 1 hour. Water was added thereto, the mixture was subjected to extraction using ethyl acetate, and the organic layer was washed with water and saturated saline solution. The organic layer was dried over sodium sulfate and then under reduced pressure, and the solid thus obtained was purified by reversed-phase fractionation to obtain Compound No. 18 RDHI-034(β) (55.5 mg).

$^1$H-NMR (DMSO-$d_6$) δ 0.75 (3H, s), 0.84 (5H, s), 0.95 (3H, s), 1.04-1.18 (11H, m), 1.30-1.39 (9H, m), 1.59 (2H, m), 1.71-1.88 (5H, m), 2.10 (2H, d, J=8.8 Hz), 2.43 (1H, s), 2.68 (1H, d, J=9.2 Hz), 3.81 (1H, t, J=8.8 Hz), 5.50 (1H, s), 6.78 (1H, s), 7.14 (1H, s), 7.45-7.51 (5H×1/2, m), 7.81-7.89 (5H×1/2, m)

Calcd for $C_{37}H_{52}N_2O_3$: 572.40, Found: 573.64, [M+$^{1-1}$], (positive-ESI).

Example 19: Example 19: Synthesis of Compound No. 19 RDHI-035(α)

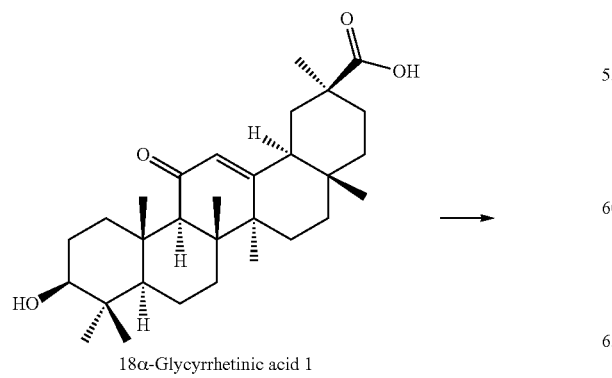

18α-Glycyrrhetinic acid 1

-continued

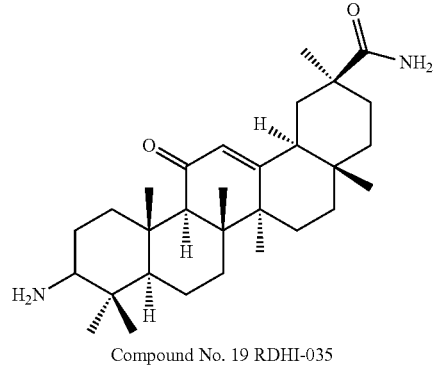

Compound No. 19 RDHI-035

Compound No. 19 RDHI-035(α) (25.1 mg) was synthesized from 18α-glycyrrhetinic acid 1 by the same method as for Compound No. 16 RDHI-032(β).

$^1$H-NMR (DMSO-$d_6$) δ 0.66 (3H, s), 0.70 (2H, d, J=12.4 Hz), 0.74 (3H, s), 0.90 (3H, s), 1.03-1.12 (11H, m), 1.23-1.42 (9H, m), 1.56 (5H, m), 1.75-1.87 (2H, m), 1.98 (2H, m), 2.20 (1H, dd, J=4.4 Hz, 10.0 Hz), 2.33 (1H, s), 2.58 (1H, d, J=12.4 Hz), 5.47 (1H, s), 6.77 (1H, s), 7.13 (1H, s)

Calcd for $C_{30}H_{48}N_2O_2$: 468.37, Found: 469.49, [M+H], (positive-ESI).

Example 20: Example 20: Synthesis of Compound No. 20 RDHI-039(α)

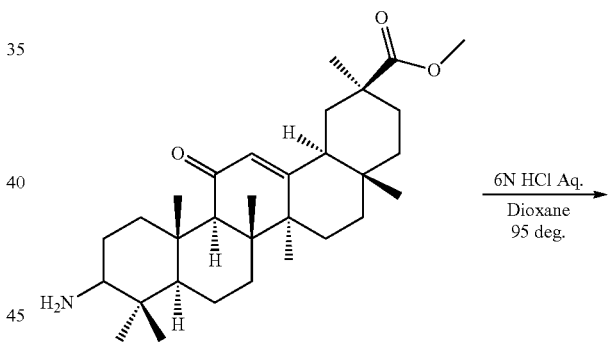

Compound No. 1 (RDHI-012)(α)

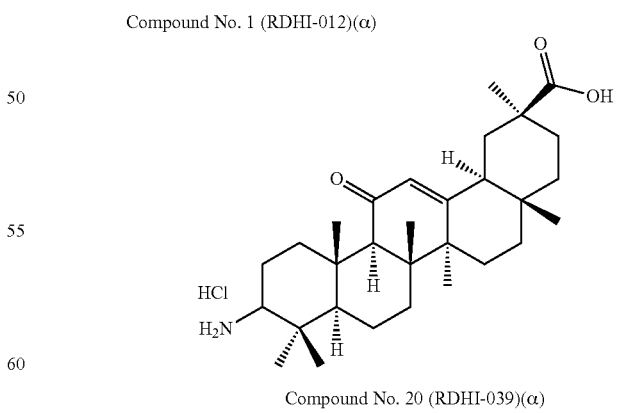

Compound No. 20 (RDHI-039)(α)

Dioxane (1.5 mL), water (0.75 mL), and concentrated hydrochloric acid (0.75 mL) were added to Compound No. 1 (RDHI-012)(α) (75 mg), the mixture was hermetically enclosed in the container and stirred at 95° C. through the night. The reaction solution was concentrated and slurry-washed with acetonitrile to obtain Compound No. 20 RDHI-039 (u) (46 mg).

¹H-NMR (DMSO-d₆) δ 0.65 (3H, s), 0.72 (1H, s), 0.77 (1H, s), 0.78 (3H, s), 0.85-0.92 (3H, m), 1.01 (3H, s), 1.05 (3H, s), 1.10 (3H, s), 1.16 (3H, s), 1.22-1.47 (5H, m), 1.34 (3H, s), 1.50-1.56 (2H, m), 1.61-1.69 (2H, m), 1.75-1.79 (1H, m), 1.89-1.91 (1H, m), 1.99-2.10 (1H, m), 2.27-2.33 (2H, m), 2.73-2.83 (1H, m), 2.90-3.01 (1H, m), 3.08-3.17 (1H, m), 5.35 (1H, s), 7.83 (2H, s) Calcd for $C_{30}H_{47}NO_3$ (Free base): 469.71, Found: 470.45, [M+H], (positive-ESI).

Example 21: Example 21: Synthesis of Compound No. 21 RDHI-040(β)

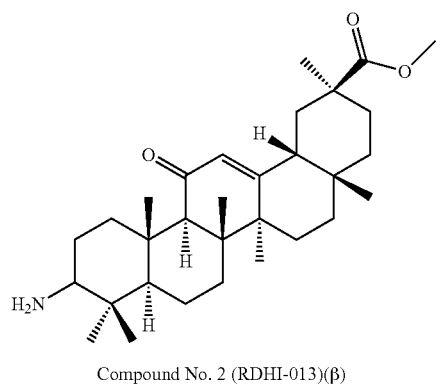

Compound No. 2 (RDHI-013)(β)

6N HCl Aq.
Dioxane
95 deg.

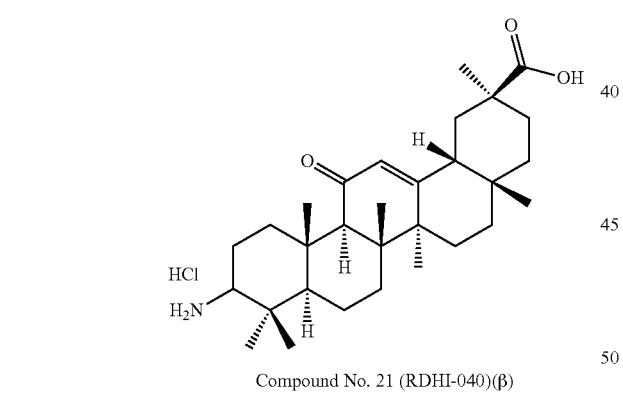

Compound No. 21 (RDHI-040)(β)

Compound No. 21 RDHI-040(β) (54 mg) was synthesized from Compound No. 2 by the same method as for Compound No. 20 RDHI-039(α).

¹H-NMR (DMSO-d₆) δ 0.65 (3H, s), 0.72 (1H, s), 0.75-0.78 (1H, m), 0.78 (3H, s), 1.01 (3H, s), 1.05 (3H, s), 1.10 (3H, s), 1.16 (3H, s), 1.19-1.49 (5H, m), 1.35 (3H, s), 1.49-1.59 (2H, m), 1.59-1.72 (2H, m), 1.73-1.84 (1H, m), 1.84-1.96 (1H, m), 1.98-2.13 (1H, m), 2.25-2.37 (2H, m), 2.72-2.85 (2H, m), 2.88-3.02 (1H, m), 5.35 (1H, s), 7.79 (2H, s), 12.18 (1H, s)

Calcd for $C_{30}H_{47}NO_3$: 469.71 (Free base), Found: 470.45, [M+H], (positive-ESI).

Example 22: Example 22: Synthesis of Compound No. 22 RDHI-041(α)

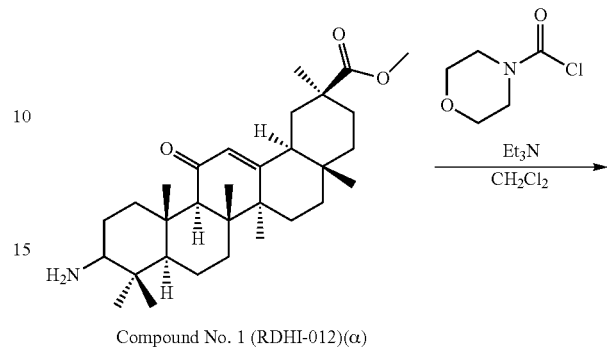

Compound No. 1 (RDHI-012)(α)

Et₃N
CH₂Cl₂

Compound No. 22 (RDHI-041)(α)

Compound No. 1 (RDHI-012)(α) (50 mg) was dissolved in dichloromethane (2.0 mL), triethylamine (12.5 mg) and 4-morpholinyl carbonyl chloride (18.5 mg) were added to the solution, and the mixture was stirred at room temperature through the night. Chloroform was added to the reaction solution, and the mixture was sequentially washed with water, saturated sodium bicarbonate water, and saturated saline solution. The organic layer was dried over sodium sulfate and then concentrated to obtain a crude product. The crude product was purified by HPLC fractionation (water [0.05% TFA]/acetonitrile [0.05% TFA]=90/10 to 1/99) using an ODS column to obtain Compound No. 22 RDHI-041(α) (45 mg).

¹H-NMR (DMSO-d₆) δ 0.73 (3H, s), 0.75 (3H, s), 0.77 (3H, s), 0.81-0.90 (2H, m), 1.04 (3H, s), 1.05 (3H, s), 1.11 (3H, s), 1.13-1.30 (2H, m), 1.30-1.59 (6H, m), 1.38 (3H, s), 1.59-1.79 (4H, m), 1.83 (1H, d, J=12.8 Hz), 2.00 (1H, t, J=8.4 Hz), 2.10 (1H, dt, J=4.0 Hz, 12.8 Hz), 2.40 (1H, s), 2.61 (1H, d, J=13.2 Hz), 3.15-3.49 (8H, m), 3.53 (1H, t, J=5.2 Hz), 3.64 (3H, s), 5.43 (1H, s), 5.83 (1H, d, J=9.2 Hz)

Calcd for $C_{36}H_{56}N_2O_5$: 596.85, Found: 597.63, [M+H], (positive-ESI).

Example 23: Example 23: Synthesis of Compound No. 23 RDHI-042(β)

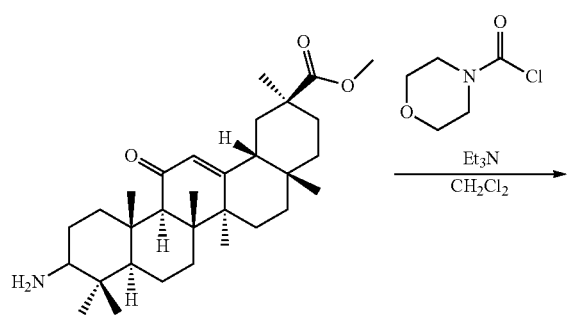

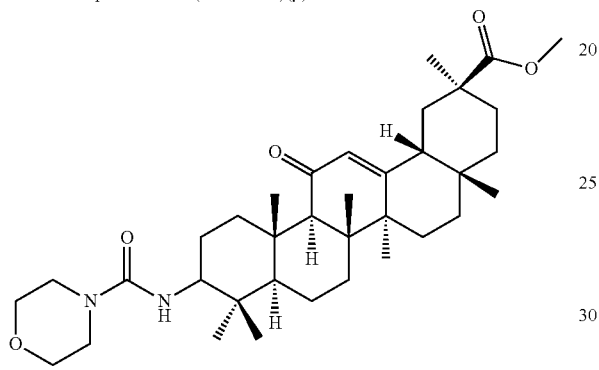

Compound No. 23 (RDHI-042)(β)

Compound No. 23 RDHI-042(β) (44 mg) was synthesized from Compound No. 2 by the same method as for Compound No. 22 RDHI-041(α).

$^1$H-NMR (DMSO-d$_6$) δ 0.73 (3H, s), 0.75 (3H, s), 0.77 (3H, s), 0.81-0.90 (2H, m), 1.04 (3H, s), 1.05 (3H, s), 1.11 (3H, s), 1.13-1.30 (2H, m), 1.30-1.59 (6H, m), 1.38 (3H, s), 1.59-1.79 (4H, m), 1.83 (1H, d, J=12.8 Hz), 2.00 (1H, t, J=8.0 Hz), 2.10 (1H, dt, J=4.4 Hz, 8.8 Hz), 2.40 (1H, s), 2.61 (1H, d, J=13.2 Hz), 3.15-3.49 (8H, m), 3.53 (1H, t, J=5.6 Hz), 3.64 (3H, s), 5.43 (1H, s), 5.82 (1H, d, J=9.2 Hz)

Calcd for $C_{36}H_{56}N_2O_5$: 596.85, Found: 597.63, [M+H]$_r$ (positive-ESI).

Example 24: Example 24: Synthesis of Compound No. 24 RDHI-043(α)

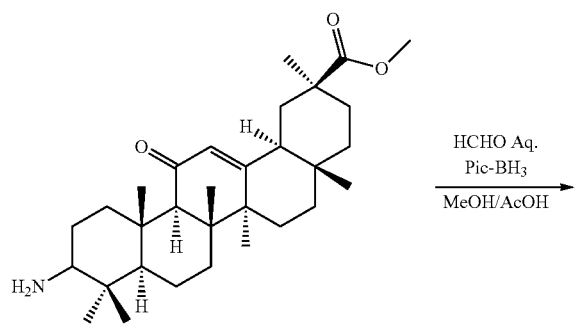

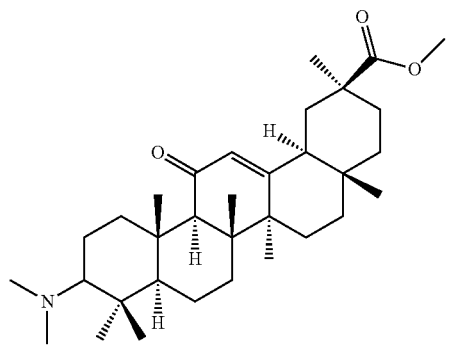

Compound No. 24 (RDHI-043)(α)

Compound No. 1 (RDHI-012)(α) (75 mg) was dissolved in methanol (1.5 mL), acetic acid (0.150 mL), 37% aqueous formaldehyde solution (0.0302 mL), and 2-picoline borane (49.7 mg) were added to the solution, and the mixture was stirred at room temperature through the night. The reaction mixture was concentrated, then saturated sodium bicarbonate water was added thereto, and the solid thus generated was washed with water and ethyl acetate to obtain Compound No. 24 RDHI-043(α) (58 mg).

$^1$H-NMR (DMSO-d$_6$) δ 0.75 (3H, s), 0.79-1.01 (5H, m), 1.05 (3H, s), 1.08 (3H, s), 1.11 (3H, s), 1.12-1.28 (5H, m), 1.29-1.60 (6H, m), 1.35 (3H, s), 1.60-1.90 (5H, m), 1.72 (2H, d, J=8.8 Hz), 2.01 (1H, t, J=7.2 Hz), 2.10 (1H, dt, J=3.2 Hz, 10.0 Hz), 2.36 (1H, s), 2.67 (3H, t, J=2.4 Hz), 2.71-2.80 (1H, m), 2.83 (3H, d, J=3.2 Hz), 2.95-3.05 (1H, m), 3.64 (3H, s), 5.45 (1H, s)

Calcd for $C_{33}H_{53}NO_3$: 511.79, Found: 512.51, [M+H] (positive-ESI).

Example 25: Example 25: Synthesis of Compound No. 25 RDHI-044(β)

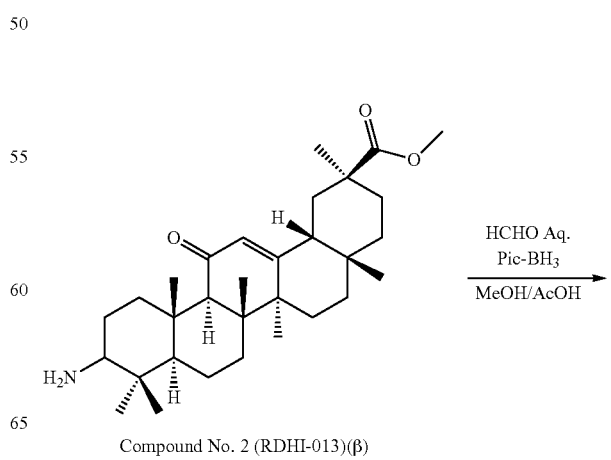

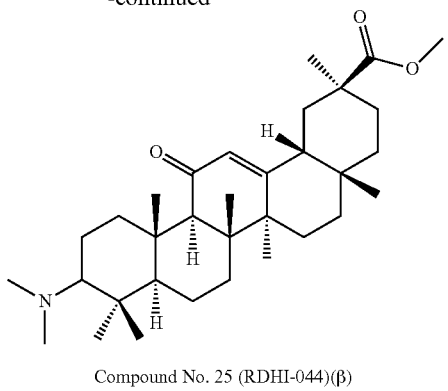

Compound No. 25 (RDHI-044)(β)

Compound No. 25 RDHI-044(β) (37 mg) was synthesized from Compound No. 2 by the same method as for Compound No. 24 RDHI-043(α).

$^1$H-NMR (DMSO-d$_6$) δ 0.75 (3H, s), 0.79-1.00 (2H, m). 1.02 (3H, s), 1.04 (3H, s), 1.08 (3H, s), 1.11 (3H, s), 1.12-1.29 (5H, m), 1.29-1.60 (6H, m), 1.35 (3H, s), 1.60-1.88 (5H, m), 1.72 (2H, d, J=9.2 Hz), 2.01 (1H, t, J=8.4 Hz), 2.05-2.15 (1H, m), 2.35 (1H, s), 2.67 (3H, t, J=2.0 Hz), 2.71-2.79 (1H, m), 2.79-2.92 (3H, m), 2.95-3.06 (1H, m), 3.64 (3H, s), 5.44 (1H, s)

Calcd for C$_{33}$H$_{53}$NO$_3$: 511.79, Found: 512.51, [M+H], (positive-ESI).

Example 26: Example 26: Synthesis of Compound No. 26 RDHI-045(α)

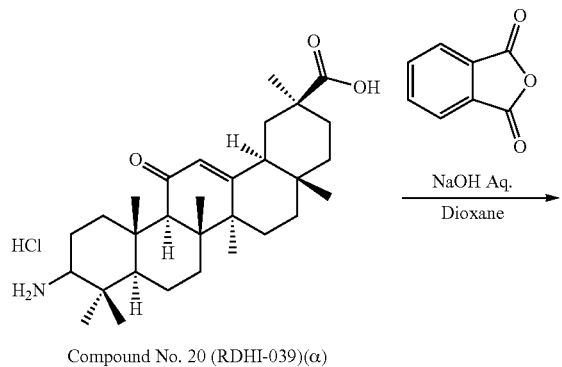

Compound No. 26 (RDHI-045)(α)

Dioxane (1.0 mL), 1 M aqueous sodium hydroxide solution (0.18 mL), and phthalic anhydride (19.5 mg) were added to Compound No. 20 (RDHI-039)(α) (60 mg), and the mixture was stirred at room temperature for 1 hour. The pH of the reaction mixture was adjusted to about 3 with 1 M hydrochloric acid, and then the reaction mixture was subjected to extraction using ethyl acetate. The organic layer was washed with saturated saline solution, dried over sodium sulfate, and then concentrated to obtain a crude product. The crude product was purified by HPLC fractionation (water [0.05% TFA]/acetonitrile [0.05% TFA]=90/10 to 1/99) using an ODS column to obtain Compound No. 26 RDHI-045(α) (64.4 mg).

$^1$H-NMR (DMSO-d$_6$) δ 0.61 (3H, s), 0.73 (3H, s), 0.85-0.92 (2H, m), 0.90 (3H, s), 1.02-1.32 (2H, m), 1.06 (3H, s), 1.12 (3H, s), 1.17 (3H, s), 1.32-1.45 (9H, m), 1.49-1.61 (3H, m), 1.61-1.73 (3H, m), 1.74-1.85 (1H, m), 1.85-1.97 (1H, m), 2.00-2.15 (1H, m), 2.24-2.35 (1H, m), 2.38 (1H, s), 3.69 (1H, dt, J=4.4 Hz, 12.0 Hz), 5.35 (1H, s), 5.42 (1H, s), 7.35 (1H, d, J=7.2 Hz), 7.48 (1H, dt, J=1.6 Hz, 7.2 Hz), 7.56 (1H, dt, J=2.0 Hz, 7.6 Hz), 7.76 (1H, dd, J=2.0 Hz, 8.0 Hz), 7.89 (1H, d, J=10.0 Hz)

Calcd for C$_{38}$H$_{51}$NO$_6$: 617.83, Found: 618.81, [M+H], (positive-ESI).

Example 27: Example 27: Synthesis of Compound No. 27 RDHI-046(β)

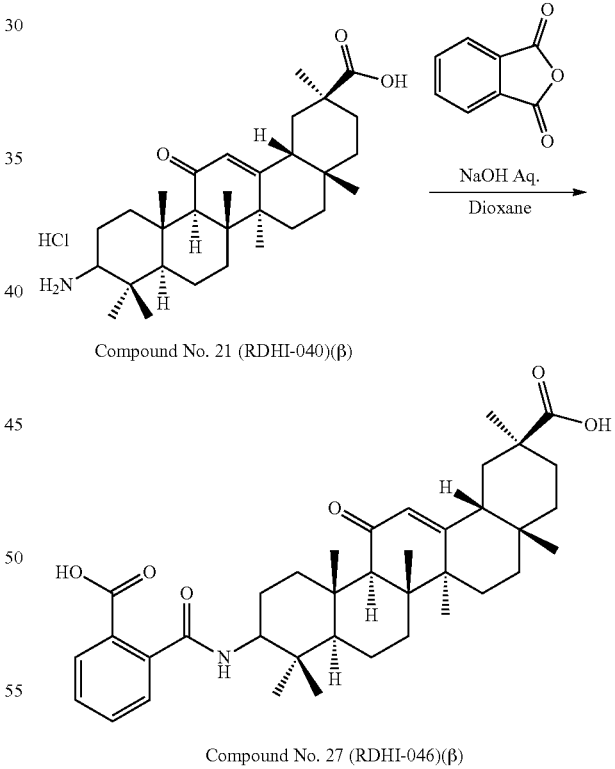

Compound No. 27 (RDHI-046)(β)

Dioxane (1.0 mL), 1 M aqueous sodium hydroxide solution (0.239 mL), and phthalic anhydride (12.9 mg) were added to Compound No. 21 (RDHI-040)(β)(40 mg), and the mixture was stirred at room temperature for 3 hours. The pH of the reaction mixture was adjusted to about 3 with 1 M hydrochloric acid, and then the reaction mixture was subjected to extraction using ethyl acetate. The organic layer was washed with saturated saline solution, dried over sodium sulfate, and then concentrated to obtain a crude product. The crude product was purified by HPLC fractionation (water [0.05% TFA]/acetonitrile [0.05% TFA]=90/10 to 1/99) using an ODS column to obtain Compound No. 27 RDHI-046(β) (22 mg).

$^1$H-NMR (DMSO-d$_6$) δ 0.66 (3H, s), 0.76 (3H, s), 0.90 (2H, d, J=7.2 Hz), 0.93 (3H, s), 1.01-1.27 (2H, m), 1.05 (3H, s), 1.12 (3H, s), 1.17 (3H, s), 1.32-1.45 (9H, m), 1.45-1.60 (3H, m), 1.60-1.72 (3H, m), 1.74-1.84 (1H, m), 1.88-2.01 (1H, m), 2.03-2.13 (1H, m), 2.25-2.36 (1H, m), 2.38 (1H, s), 3.63-3.75 (1H, m), 5.35 (1H, s), 5.39 (1H, s), 7.35 (1H, d, J=7.6 Hz), 7.47 (1H, dt, J=1.2 Hz, 7.6 Hz), 7.54 (1H, dt, J=1.2 Hz, 7.6 Hz), 7.76 (1H, dd, J=2.4 Hz, 7.6 Hz), 7.89 (1H, d, J=10.0 Hz)

Calcd for $C_{38}H_{51}NO_6$: 617.83, Found: 618.58, [M+H], (positive-ESI).

Example 28: Example 28: Inhibition of Retinol Dehydrogenase 10 (RDH10) Enzyme Activity by Compound of Present Invention (1) Method for Measuring RDH10 Inhibitory Activity (a) Confirmation of Presence of RDH10 in Microsomal Fraction The 293T cell line (1×10$^6$) and activated human CD4$^+$T cells (1×10$^7$) were thoroughly washed with PBS and then suspended in 600 μl of 0.25 M sucrose-0.1 M sodium phosphate buffer (pH7.4). After the cell suspension was homogenized and centrifuged under conditions of 10000 g, 10 minutes, and 4° C., the supernatant was centrifuged under conditions of 100000 g, 1 hour, and 4° C. to obtain a microsomal fraction. The microsomal fraction was suspended in 20 μl of 0.1 M sodium phosphate buffer (pH7.4) and used in Western blot.

The RDH10 protein contained in the microsomal fraction was separated by SDS-PAGE, then transferred and blocked on a PVDF membrane, then reacted with an anti-RDH10 antibody (ab87586) as a primary antibody and an anti-rabbit IgG-HRP antibody as a secondary antibody, and detected using Luminata Forte Western HRP Substrate (manufactured by MilliporeSigma).

(b) Measurement of RDH10 Enzyme Activity

All-trans retinol, BSA, and NAD (nicotinamide adenine dinucleotide) as a coenzyme were added to a buffer for reaction (90 mM potassium phosphate buffer, pH7.4, 40 mM KCl) so as to have final concentrations of 10 μM, 10 μM, and 1 mM respectively. This mixture was taken in siliconized tubes by 200 μl for each, the microsomal fractions separated from 293T and RDH10-expressed 293T were added to separate tubes by 10 μl for each, and the mixtures were allowed to react at 37° C. for 15 minutes. After 200 μl of methanol was added to the reaction mixtures to stop the reaction, retinoid was extracted using hexane and concentrated. The concentrated retinoid was dissolved in 150 μl of acetonitrile, separated by HPLC, and subjected to the detection of ultraviolet light absorption at a wavelength of 350 nm, whereby the substrate (all-trans retinol) and the product (all-trans retinal) were detected. In addition, standard samples (all-trans retinol and all-trans retinal) were separated by HPLC and the retention times of the respective standard samples were determined in advance. The solvent for HPLC was acetonitrile: 50 mM ammonium acetate=75:25. As the separation column, Syhergi 4 μm Hydro-RP 80A (manufactured by Phenomenex) was used. In addition, the flow rate was 2.0 ml/min. The RDH10 enzyme activity was calculated by reading the amount of product per fixed time from the chart of HPLC.

(c) Inhibition of RDH10 Enzyme Activity by Compound of Present Invention

All-trans retinol, BSA, and NAD (nicotinamide adenine dinucleotide) as a coenzyme were added to a buffer for reaction (90 mM potassium phosphate buffer, pH7.4, 40 mM KCl) so as to have final concentrations of 10 μM, 10 μM, and 1 mM respectively. This mixture was taken in siliconized tubes by 200 μl for each, the microsomal fraction separated from RDH10-expressed 293T was added to separate tubes by 10 μl for each. The RDH10 inhibitor dissolved in DMSO was added to each tube so as to have a final concentration of 20 μM, and the same amount of DMSO was added to the control tube. The mixture was allowed to react at 37° C. for 15 to 30 minutes, 200 μl of methanol was added to the reaction mixtures, and then retinoid was extracted using hexane and concentrated. The concentrated retinoid was dissolved in 150 μl of acetonitrile, separated by HPLC, and subjected to the detection of ultraviolet light absorption at a wavelength of 350 nm, whereby the substrate (all-trans retinol) and the product (all-trans retinal) were detected. In addition, standard samples (all-trans retinol and all-trans retinal) were separated by HPLC and the retention times of the respective standard samples were determined in advance. The solvent for HPLC was acetonitrile: 50 mM ammonium acetate=75:25. As the separation column, Syhergi 4 μm Hydro-RP 80A (manufactured by Phenomenex) was used. The flow rate was 2.0 ml/min.

The enzyme activity was determined by the waveform area of the product (all-trans retinal) with respective to the waveform area of the non-reacted substrate (all-trans retinol), and the relative value with respect to the enzyme activity in the control is illustrated in FIG. 1. The error bars indicate SD (standard deviation).

It has been confirmed that the compounds of the present invention inhibit RDH10 enzyme activity. Among these, Compounds Nos. 1 (RDHI-012), 2 (RDHI-013), 5 (RDHI-016), 9 (RDHI-023), 10 (RDHI-024), 14 (RDHI-028), 16 (RDHI-032), 17 (RDHI-033), and 18 (RDHI-034) exhibited relatively potent RDH enzyme activity inhibitory action, and in particular, Compounds Nos. 1 (RDHI-012) and 2 (RDHI-013) exhibited potent RDH10 enzyme activity inhibitory action. In addition, Compounds RDHI-041 and 042 were also exhibited the RDH10 enzyme activity inhibitory action.

Example 29: Example 29: Effect of Compound of Present Invention In Vitro

Healthy human-derived CD4$^+$CD45RO$^+$T cells (1×10$^5$) were cultured in the presence of anti-CD3 antibody (2 μg/ml), anti-CD28 antibody (2 μg/ml), IL-2 (20 IU/ml) and RDH10 inhibitors (Compound No. 16 (RDHI-032), Compound No. 17 (RDHI-033), and Compound No. 18 (RDHI-034)) (20 μM for each). In addition, DMSO was used as a control for the RDH10 inhibitor. After seven days from the start of resuspended in a fresh culture medium to which IL-2 was not added, and cultured for one more day. Thereafter, the expression of CD62L and CD127 in T cells was analyzed by flow cytometry. The culture solution used was X-VIVO15 to which AB serum was added to have a final concentration of 10%.

Figure 2:
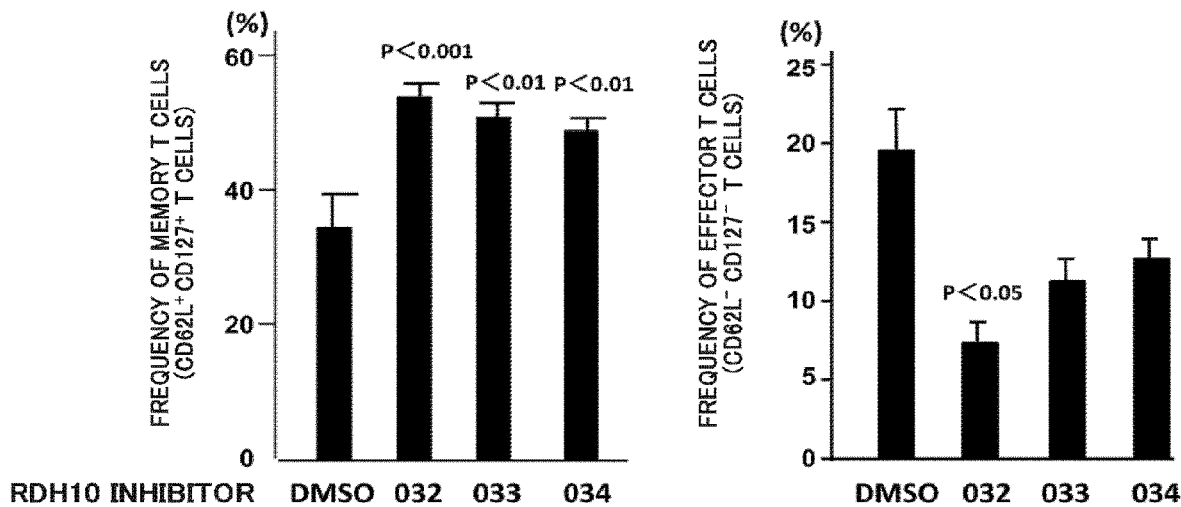
FIG. 2 is a graph illustrating the amplification of memory T cells and a decrease in effector T cells by a compound of the present invention. The compound is denoted by the applicant's reference number (RDHI-No.).

The results are illustrated in FIG. 2. All the RDH10 inhibitors (Compound No. 16 (RDHI-032), Compound No. 17 (RDHI-033), and Compound No. 18 (RDHI-034)) amplified memory T cells (CD62L$^+$CD127$^+$T cells), and as a result, effector T cells (CD62L$^-$CD127$^-$T cells) decreased.

In addition, Compounds RDHI-014, 016, 017, 025, 026, 035, 036, 038, 039, 040, 041, 042, and 046 also tended to amplify memory cells.

Example 30: Example 30: Effect of Compound of Present Invention In Vivo

Figure 3:
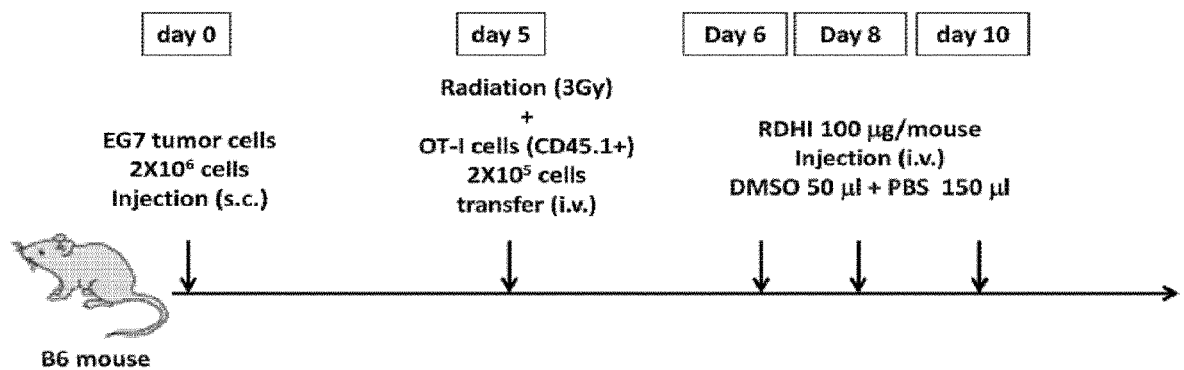
FIG. 3 is a scheme illustrating the procedure of an experiment for examining an effect in vivo by a compound of the present invention.

A mouse cancer cell line EG7 ($2\times10^6$) expressing OVA (chicken ovalbumin) was subcutaneously injected into C57BL/6J mouse (B6 mouse) to form a tumor. Five days later, the mouse in which a tumor was formed was irradiated with radiation at 3 Gy, then T cell-receptive OTCD8$^+$T cells (OT-1 cells) specific for OVA antigen were isolated from CD45.1 positive OT-I transgenic mouse, and this was transferred into the mouse by $2\times10^5$ through the tail vein. A total of 3 times every other day from the next day, RDH10 inhibitors (Compound No. 1 (RDHI-012) and Compound No. 2 (RDHI-013)) were administered to the mouse at 100 µg/mouse for each through the tail vein. The RDH10 inhibitors were administered to the mouse by being previously stocked in DMSO at 100 µg/50 µl and adjusted to have a total volume of 200 µl by the addition of 150 µl of PBS. These procedures are summarized in FIG. 3.

In the experiment, tumor volumes were measured over time. The frequency of OT-1 cells (OVA specific CD8$^+$T cells) in peripheral blood on the 20th day was measured. Furthermore, the expression intensity of cell surface antigen molecules (CD62L, CD127), which were markers of memory T cells, was analyzed.

Figure 4:
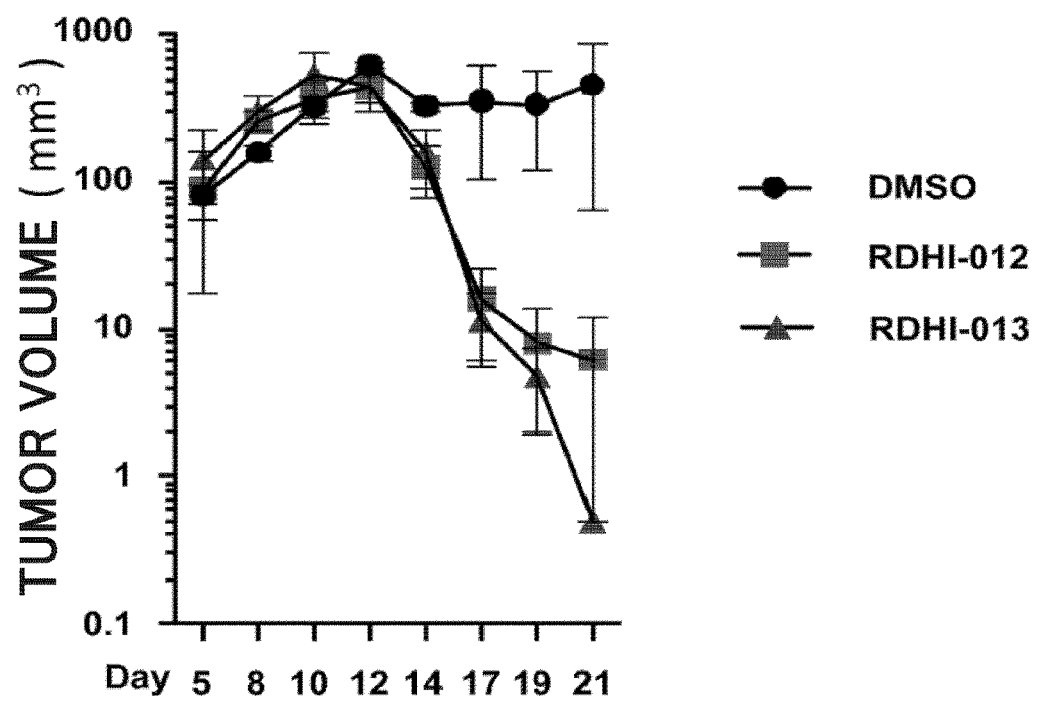
FIG. 4 is a graph illustrating an effect of inhibiting tumor growth in vivo by a compound of the present invention over time. The compound is denoted by the applicant's reference number (RDHI-No.).

The time course in the mean value of tumor volume after tumor transplantation is illustrated in FIG. 4. The error bars indicate the standard error. The tumor volume was determined by major axis×minor axis×height/2. The tumor volume increased to the 12th day after tumor transplantation, but, thereafter, the tumor volume decreased in animals to which the RDH10 inhibitors (Compound No. 1 (RDHI-012) and Compound No. 2 (RDHI-013)) were administered, and the tumor volume decreased to one several tenths to one several hundredths on the 21st day after transplantation.

From these results, it has been confirmed that the RDH10 inhibitors (Compound No. 1 (RDHI-012) and Compound No. 2 (RDHI-013)) suppress the proliferation of tumor in vivo.

Figure 5:
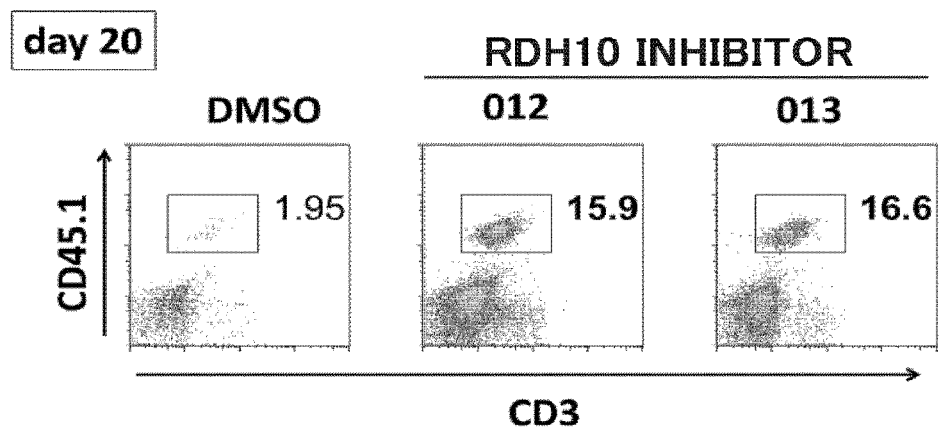
FIG. 5 is a diagram illustrating the results of flow cytometry showing the amplification of CD45.1$^+$OT-1 cells (OVA specific CD8$^+$ cells) in vivo by a compound of the present invention. The compound is denoted by the applicant's reference number (RDHI-No.).

On the 20th day after the tumor transplantation, the frequency of transferred OT-I cells contained in peripheral blood was analyzed by flow cytometry. OT-I cells were CD45.1 positive and thus were clearly distinguishable from the host B6 mouse (CD45.2 positive)-derived T cells. The representative results are illustrated in FIG. 5. From these results, it has been confirmed that the RDH10 inhibitors (Compound No. 1 (RDHI-012) and Compound No. 2 (RDHI-013)) amplify CD45.1$^+$OT-1 cells (OVA specific CD8$^+$ cells) in vivo.

Figure 6:
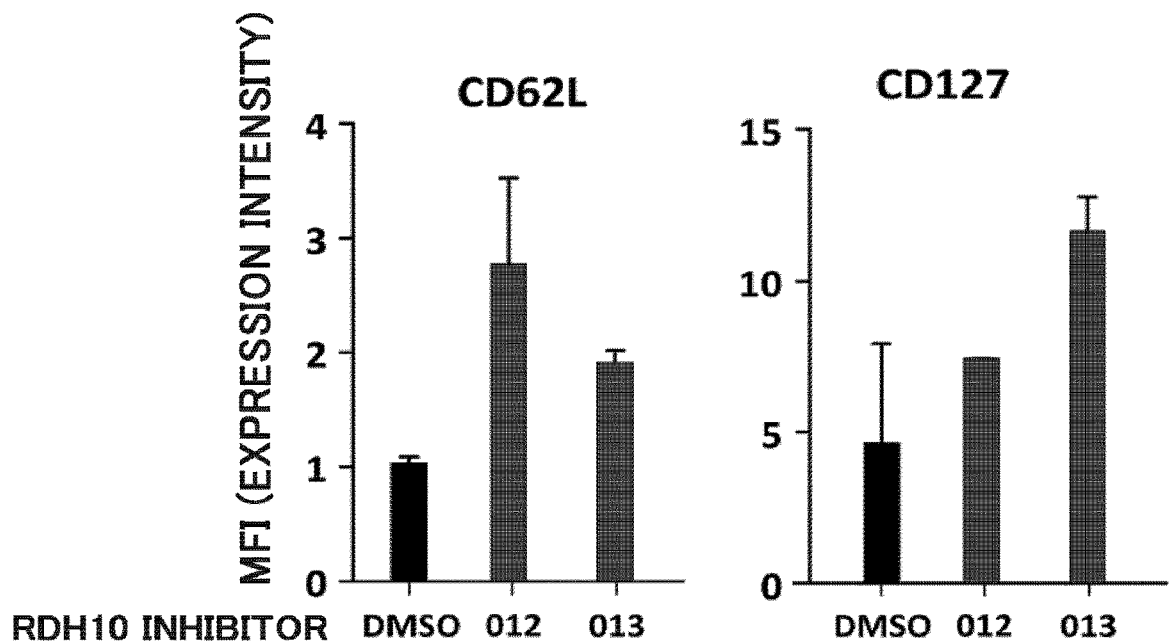
FIG. 6 is a graph illustrating the results of flow cytometry analysis for expression intensities of CD62L and CD127 in OT-I cells illustrated in FIG. 5. The compound is denoted by the applicant's reference number (RDHI-No.).

The expression intensities of CD62L and CD127 in OT-I cells illustrated in FIG. 5 were analyzed by flow cytometry. The mean value and standard error of each expression intensity are illustrated in FIG. 6. From these results, it has been confirmed that the RDH10 inhibitors (Compound No. 1 (RDHI-012) and Compound No. 2 (RDHI-013)) accelerate the expression of CD62L and CD127, which are molecular markers of memory-type T cells in CD45.1$^+$OT-1 cells (OVA specific CD8$^+$ cells) amplified in vivo.

INDUSTRIAL APPLICABILITY

According to the present invention, a method for increasing the proportion of memory T cells in a T cell population using an inhibitory substance of retinoid metabolic pathway, a preventive and/or therapeutic agent for cancer or an infectious disease containing the inhibitory substance, an adjuvant for cancer immunotherapy containing the inhibitory substance, an immunity enhancer containing the inhibitory substance, and the like are provided. These can be utilized in the fields of medicines and the like, for example, in the fields of development and manufacture of medicines for the prevention and/or treatment of various diseases including cancer and infectious diseases and methods for treating the diseases, in particular the development of immunotherapy.

Sequence Listing

The invention claimed is:

1. A compound selected from the group consisting of (2S,4aS,6aS,6bR,8aR,12aS,12bR,14bS)-methyl 10-(3-(2-(methoxycarbonyl)phenyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 9 (RDHI-023)), (2S,4aS,6aS,6bR,8aR,12aS,12bR,14bS)-methyl 10-(3-(2-ethoxy-2-oxoethyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 10 (RDHI-024)), (2S)-2-(3-((4aR,6aR,6bS,8aS,11S,12aS,14aR,14bS)-11-(methoxycarbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)ureido)-3-phenyl propanoic acid (Compound No. 14 (RDHI-028)), (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 16 (RDHI-032)), (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 17 (RDHI-033)), and (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 18 (RDHI-034)), or a pharmaceutically acceptable salt of the compound.

2. The compound of claim 1, wherein the compound is (2S,4aS,6aS,6bR,8aR,12aS,12bR,14bS)-methyl 10-(3-(2-(methoxycarbonyl)phenyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 9 (RDHI-023)).

3. The compound of claim 1, wherein the compound is (2S,4aS,6aS,6bR,8aR,12aS,12bR,14bS)-methyl 10-(3-(2-ethoxy-2-oxoethyl)ureido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (Compound No. 10 (RDHI-024)).

4. The compound of claim 1, wherein the compound is (2S)-2-(3-((4aR,6aR,6b S,8aS,11 S,12aS,14aR,14b S)-11-(methoxycarbonyl)-4,4,6a,6b,8a, 11,14b-heptamethyl-14-oxo-1,2,3,4,4a,5,6,6a,6b,7,8,8a,9,10,11,12,12a,14,14a,14b-icosahydropicen-3-yl)ureido)-3-phenyl propanoic acid (Compound No. 14 (RDHI-028)).

5. The compound of claim 1, wherein the compound is (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 16 (RDHI-032)).

6. The compound of claim 1, wherein the compound is (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 17 (RDHI-033)).

7. The compound of claim 1, wherein the compound is (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 18 (RDHI-034)).

8. A method for producing a T cell population having an increased proportion of a memory T cell, comprising:
   mixing a compound or a pharmaceutically acceptable salt thereof with a T cell population such that the T cell population has an increased proportion of a memory T cell,
   wherein the compound is selected from the group consisting of
   (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 16 (RDHI-032)),
   (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 17 (RDHI-033)), and
   (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 18 (RDHI-034)).

9. The method of claim 8, wherein the compound is (2S,4aS,6aS,6bR,8aR,12aS,12bR,14bR)-10-amino-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 16 (RDHI-032)).

10. The method of claim 8, wherein the compound is (2S,4aS,6aS,6bR,8aR,12aS,12bR,14bR)-10-acetamido-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 17 (RDHI-033)).

11. The method of claim 8, wherein the compound is (2S,4aS,6aS,6bR,8aR,12aS,12bR,14bR)-10-benzamide-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxamide (Compound No. 18 (RDHI-034)).

\* \* \* \* \*